(12) United States Patent
Rege et al.

(10) Patent No.: US 7,439,343 B2
(45) Date of Patent: Oct. 21, 2008

(54) AMINOGLYCOSIDE-POLYAMINE DISPLACERS AND METHODS OF USE IN DISPLACEMENT CHROMATOGRAPHY

(75) Inventors: Kaushal Rege, Troy, NY (US); Shanghui Hu, San Diego, CA (US); Jonathan S. Dordick, Schenectady, NY (US); Steven M. Cramer, Niskayuna, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 267 days.

(21) Appl. No.: 11/217,193

(22) Filed: Sep. 1, 2005

(65) Prior Publication Data

US 2007/0049741 A1  Mar. 1, 2007

(51) Int. Cl.
C07H 1/06 (2006.01)
C07H 15/20 (2006.01)
C07H 17/00 (2006.01)

(52) U.S. Cl. .................... 536/17.4; 536/13.6; 536/13.7; 536/13.8; 536/17.9; 536/127

(58) Field of Classification Search ................ 536/13.7, 536/13.8, 17.4, 17.9
See application file for complete search history.

(56) References Cited

U.S. PATENT DOCUMENTS

| | | | |
|---|---|---|---|
| 4,028,188 A | 6/1977 | Daum et al. | |
| 4,217,446 A | 8/1980 | Moore | |
| 4,230,847 A | 10/1980 | Nagabhushan et al. | |
| 5,039,666 A | 8/1991 | Novick, Jr. | |
| 6,180,612 B1 | 1/2001 | Hockensmith et al. | |
| 6,699,848 B1 * | 3/2004 | Barbeau ...................... | 514/54 |

OTHER PUBLICATIONS

Boger et al., "A Simple, High-Resolution Method for Establishing DNA Binding Affinity and Sequence Selectivity", *J of Am. Chem. Soc.*, 123, pp. 5878-5891 (2001).
Ferreira et al., "Exquisite Regioselectivity and Increased Transesterification Activity of an Immobilized *Bacillus subtilis* Protease", *Biotechnol. Prog.*, 18, pp. 986-993 (2002).
Garcia-Alles et al. "Synthesis of Purine and Pyrimidine 3'-Amino-3'-deoxy- and 3'-Amino-2',3'-dideoxyxylonucleosides", *J. of Amer. Chem. Soc.*, 61, pp. 6980-6986 (1996).
Geall et al., "Rapid and Sensitive Ethidium Bromide Fluorescence Quenching Assay of Polyamine Conjugate-DNA Interactions for the Analysis of Lipoplex Formation in Gene Therapy", *J. of Pharm. Biomed. Analysis*, 22, pp. 849-859 (2000).
Hennen, et al., "Enzymes in Carbohydrate Synthesis: Lipase-Catalyzed Selective Acylation and Deacylation of Furanose and Pyranose Derivatives", *J. Org. Chem*, 1988, 53, pp. 4939-4945.
Jayaraman et al., "Ion-Exchange Displacement Chromatography of Proteins: Dendritic Polymers as Novel Displacers", *J. of Amer. Chromatography*, 702, pp. 143-155 (1995).

Kundu et al., "Protected Amino Acids as Novel Low-Molecular-Weight Displacers in Cation-Exchange Displacement Chromatography", *Biotechnology and Bioengineering*, 48, pp. 452-460 (1995).
Kundu et al., "Antibiotics as Low Molecular Weight Displacers in Ion Exchange Displacement Chromatography", *J. of Chromatography*, 707, 57-67 (1995).
Mazza et al., "High-Throughput Screening and Quantitative Structure-Efficacy Relationship Models of Potential Displacer Molecules for Ion-Exchange Systems", *Biotech. Bioengineering*, 80, p. 60-73 (2002).
Raspaud et al., "Spermine-Induced Aggregation of DNA, Nucleosome, and Chromatin", *Biophysical Journal*, 77, pp. 1547-1555 (1999).
Rege et al., "Predicting Column Performance in Displacement Chromatography from High Throughput Screening Batch Experiments", *Separation Science and Technology*, 38, pp. 1499-1517 (2003).
Riva, et al., "Protease-Catalyzed Regioselective Esterification of Sugars and Related Compounds in Anhydrous Dimethylformamide", *J. Am. Chem. Soc.* 1988, 110, pp. 584-589.
Saminathan et al., "Ionic and Structural Specificity Effects of Natural and Synthetic Polyamines on the Aggregation and Resolubilization of Single-, Double-, and Triple-Stranded DNA", *Biochemistry*, 38, pp. 3821-3830 (1999).
Shukla et al., "Bioseparations by Displacement Chromatography", *Handbook of Bioseparations*, vol. 1, S. Ahuja (ed.), Academic Press (2000).
Tugcu et al., "Displacement Chromatography of Anti-Sense Oligonucleotide and Proteins Using Saccharin as a Non-Toxic Displacer", *Reactive and Functional Polymers*, 54, pp. 37-47 (2003).
Tugcu et al., "Purification of an Oligonucleotide at High Column Loading by High Affinity, Low-Molecular-Mass Displacers", *Journal of Chromatography*, 923, (1-2): pp. 65-73 (2001).

* cited by examiner

*Primary Examiner*—Elli Peselev
(74) *Attorney, Agent, or Firm*—Heslin Rothenberg Farley & Mesiti P.C.

(57) ABSTRACT

Aminoglycoside-polyamines are disclosed along with methods of use thereof in displacement chromatography and as DNA-binding ligands. The aminoglycoside-polyamines are derivatives of carbohydrates, such as sugars, amino sugars, deoxysugars, glycosides, nucleosides and their substituted counterparts. The subject polyamines possess a

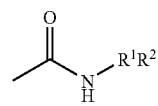

group in place of at least one hydrogen atom of at least one hydroxyl group of the carbohydrate compound. In these compounds $R^1$ is an alkyl group or an azaalkyl group, and $R^2$ is a primary or secondary amino group.

5 Claims, 3 Drawing Sheets

AMINOGLYCOSIDE-POLYAMINE DISPLACERS AND METHODS OF USE IN DISPLACEMENT CHROMATOGRAPHY

FEDERALLY SPONSORED RESEARCH

The following invention was made with Government support under contract number 0079436 awarded by the National Science Foundation and contract number GM047372 awarded by the National Institutes of Health. The Government has certain rights in this invention.

FIELD OF THE INVENTION

The invention relates to aminoglycoside-polyamines, and methods of use thereof in displacement chromatography and as DNA-binding ligands.

BACKGROUND OF THE INVENTION

Displacement chromatography has attracted significant attention as a powerful technique for the purification of biotherapeutic proteins and oligonucleotides. In particular, low molecular weight (MW<2000) displacers have been shown to have significant advantages for high-resolution protein purification. Displacement chromatography enables simultaneous concentration and purification in a single step, which is significant in the purification of biopharmaceuticals. However, the major obstacle in implementing this technique is the lack of a sufficient diversity of appropriate displacer candidates that are applicable across a wide spectrum of bioseparation demands. Low molecular weight displacers employed to date possess moderate to high affinities, yet are unable to displace highly retained proteins on a variety of hydrophilic and hydrophobic resins. Thus, a need exists to develop high affinity and selective displacers that overcome at least one of the aforementioned deficiencies.

SUMMARY OF THE INVENTION

An aspect of the present invention relates to a derivative of a carbohydrate compound selected from a sugar, an amino sugar, a deoxysugar, a glycoside, a nucleoside, a substituted sugar, a substituted amino sugar, a substituted glycoside, a substituted aminoglycoside, and a substituted nucleoside, said derivative comprising: a group of formula I

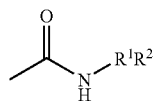

in place of at least one hydrogen atom of at least one hydroxyl group of the carbohydrate compound, or, when present, of at least one amino group of the carbohydrate compound wherein $R^1$ is an alkyl group or an azaalkyl group, and $R^2$ is a primary or secondary amino group.

A second aspect of the present invention is a method for separating one or more components of a biomolecule mixture by means of an ion exchange chromatographic system operated in the displacement mode, said method comprising: sequentially perfusing the system with a first solution comprising the biomolecule mixture, and a second solution comprising a derivative of a carbohydrate compound of formula 1 described above.

A third aspect of the present invention is a method for separating a protein or peptide mixture by means of an ion exchange chromatographic system operated in the displacement mode, said method comprising: sequentially perfusing the system with a first solution comprising said mixture, and a second solution comprising a derivative of a carbohydrate compound of formula 1.

A fourth aspect of the present invention is a method for condensing DNA, said method comprising: combining DNA with at least one derivative of a carbohydrate compound of formula 1 as described above, wherein the DNA is bound to the derivative of the carbohydrate compound.

DETAILED DESCRIPTION OF THE INVENTION

Definitions

Figure 1:
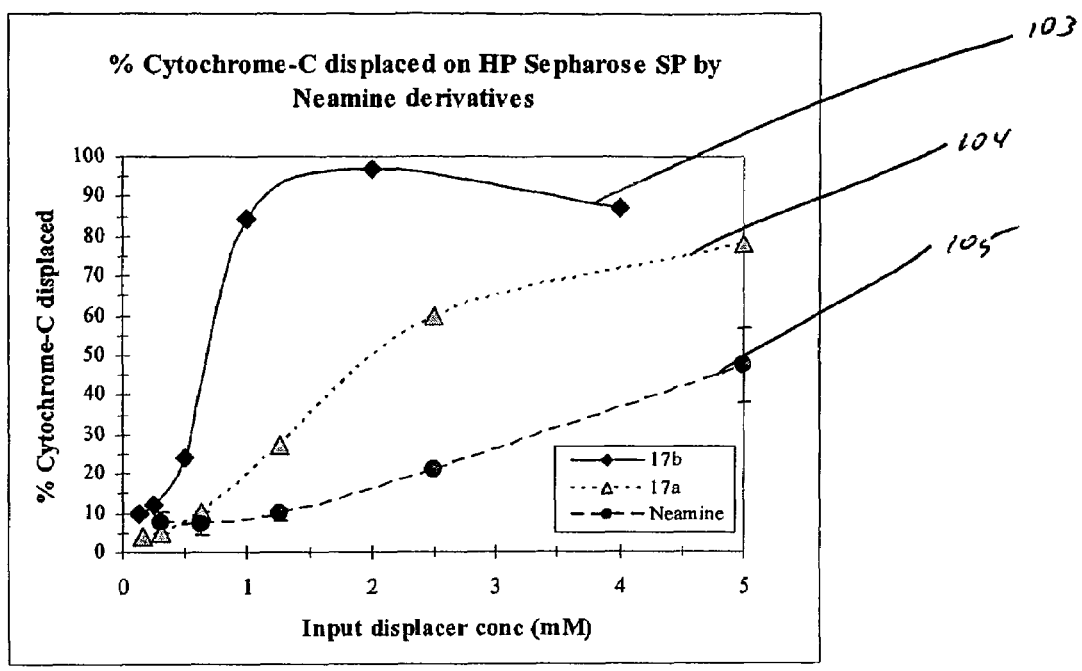
FIG. 1 depicts a graph for the displacement of cytochrome-C by various concentrations of neamine and its derivatives, in accordance with the present invention.

Throughout this specification the terms and substituents retain their definitions.

The term alkyl is intended to include a linear, a branched, or a cyclic hydrocarbon structure, and combinations thereof. A lower alkyl refers to alkyl groups having from about 1 to about 4 carbon atoms. Examples of lower alkyl groups include but are not limited to methyl, ethyl, n-propyl, isopropyl, and n-, s- and t-butyl, and the like. A cycloalkyl is a subset of alkyl and includes cyclic hydrocarbon groups having from about 3 to about 8 carbon atoms. Examples of cycloalkyl groups include but are not limited to cyclopropyl, cyclobutyl, cyclopentyl, norbornyl, and the like. Typical alkyl groups are those of $C_{20}$ or below in an embodiment of the present invention.

Examples of a $C_1$ to $C_{20}$ hydrocarbon include but are not limited to alkyl, cycloalkyl, alkenyl, alkynyl, aryl and combinations thereof. Examples include benzyl, phenethyl, cyclohexylmethyl, camphoryl and naphthylethyl. The term "phenylene" refers to ortho, meta or para residues of the formulae:

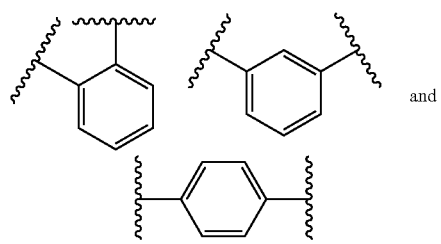

Polyol refers to a compound or residue having a plurality of —OH groups. Polyols may be thought of as alkyls in which a plurality of C—H bonds have been replaced by C—OH bonds. Common polyol compounds include for example glycerol, erythritol, sorbitol, xylitol, mannitol and inositol. Linear polyol residues will generally be of the empirical formula —$C_yH_{2y+1}O_y$, and cyclic polyol residues will generally be of the formula —$C_yH_{2y-1}O_y$. Cyclic polyols also include reduced sugars, such as glucitol.

Alkoxy or alkoxyl refers to groups having from about 1 to about 8 carbon atoms of a straight, branched, or cyclic configuration, and combinations thereof attached to the parent structure through an oxygen atom. Examples include but are not limited to methoxy, ethoxy, propoxy, isopropoxy, cyclopropyloxy, cyclohexyloxy and the like. Lower alkoxy refers to groups from about 1 to about 4 carbon atoms of a straight, branched, cyclic configuration, and combinations thereof attached to the parent structure through an oxygen atom.

Oxaalkyl refers to an alkyl residue in which one or more carbons (and their associated hydrogens) have been replaced by oxygen. Examples include methoxypropoxy, 3,6,9-trioxadecyl and the like. The term oxaalkyl is intended as it is understood in the art [see Namina and Indexina of Chemical Substances for Chemical Abstracts, published by the American Chemical Society, 1[196, but without the restriction of 1[127(a)], i.e. it refers to compounds in which the oxygen is bonded via a single bond to its adjacent atoms (forming ether bonds); it does not refer to doubly bonded oxygen, as would be found in carbonyl groups. Similarly, thiaalkyl and azaalkyl refer to alkyl residues in which one or more carbons has been replaced by sulfur or nitrogen, respectively. Examples include ethylaminoethyl and methylthiopropyl.

Acyl refers to a group having from about 1 to about 8 carbon atoms of a straight, branched, or cyclic configuration being saturated, unsaturated, or aromatic and combinations thereof, attached to the parent structure through a carbonyl functionality. One or more carbons in the acyl group may be replaced by nitrogen, oxygen or sulfur as long as the point of attachment to the parent remains at the carbonyl. Examples include acetyl, benzoyl, propionyl, isobutyryl, t-butoxycarbonyl, and benzyloxycarbonyl. Lower-acyl refers to groups containing one to four carbons.

Aryl and heteroaryl refers to a 5- or 6-membered aromatic or heteroaromatic ring containing 0-3 heteroatoms selected from nitrogen, oxygen or sulfur; a bicyclic 9- or 10-membered aromatic or heteroaromatic ring system containing 0-3 heteroatoms selected from nitrogen, oxygen or sulfur; or a tricyclic 13- or 14-membered aromatic, or heteroaromatic ring system containing 0-3 heteroatoms selected from nitrogen, oxygen or sulfur.

Examples of aromatic 6- to 14-membered carbocyclic rings include but are not limited to benzene, naphthalene, indane, tetralin, fluorine, and the like. Examples of 5- to 10-membered aromatic heterocyclic rings include but are not limited to imidazole, pyridine, indole, thiophene, benzopyranone, thiazole, furan, benzimidazole, quinoline, isoquinoline, quinoxaline, pyrimidine, pyrazine, tetrazole, pyrazole, and the like.

An arylalkyl means an alkyl residue attached an aryl ring. Examples include but are not limited to benzyl, phenethyl, and the like. Heteroarylalkyl means an alkyl group attached to a heteroaryl ring. Examples include but are not limited to pyridinylmethyl, pyrimidinylethyl, and the like. Alkylaryl means an aryl structure having one or more alkyl groups attached thereto. Examples include but are not limited to tolyl, mesityl, and the like.

Heterocycle refers to a cyclic structure or residue in which one or more of the ring atoms are replaced by an atom other than carbon. Examples include of a replacement atom includes but are not limited to oxygen, nitrogen, sulfur, and the like. Examples of heterocycles that fall within the scope of the invention include but are not limited to pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran, and the like.

Haloalkyl refers to an alkyl residue, wherein a halogen atom replaces one or more H atoms. Examples of a haloalkyl group include but are not limited to —$CH_2F$, —$CHF_2$, —$CF_3$, and the like.

Substituted refers to an alkyl, an alkoxy or alkoxyl, an oxaalkyl, an acyl, an arylalkyl, a heterocycle, a haloalkyl, or a carbohydrate, wherein one or more H atoms of the aforementioned groups or the carbohydrate is replaced with an alkyl, an alkoxy or alkoxyl, an oxaalkyl, an acyl, an arylalkyl, a heterocycle, a haloalkyl, an alkynyl, a carbonyl, a carboxy, a carboxalkoxy, a carboxamido, an acyloxy, an amidino, a nitro, a halogen, a hydroxy, an $OCH(COOH)_2$, a cyano, an amino group, an acylamino, an alkylthio, a sulfoxide, a sulfone, and the like. Examples of the substituted group, i.e. substituent, include but are not limited to phenyl, benzyl, methoxy, acetoxy, acetyl, phenoxy, and benzyloxy. Typically, an acyl, alkoxy or aryloxy group, such as OAc, OBz, or OPh, may replace one or more OH groups of the carbohydrate compound.

The term "sugar" as used in the context of the current invention is defined as listed in *Hawley's Condensed Chemical Dictionary*, 12$^{th}$ *Edition*, Richard J. Lewis, Sr.; Van Nostrand Reinhold Co. New York. The definition encompasses any carbohydrate comprised of one or two saccharose groups. Monosaccharide sugars (often called simple sugars) are composed of chains of 2-7 carbon atoms. One of the carbon atoms carries an aldehydic or ketonic oxygen, which may be combined in acetal or ketal forms. The remaining carbons usually have hydrogen atoms and hydroxyl groups. Unless specifically noted otherwise, the term "sugar" refers to both D-sugars and L-sugars.

Examples of a sugar include but are not limited to ribose, xylose, ribulose, xylulose, deoxyribose, galactose, glucose, mannose, fructose, sorbose, tagatose, fucose, quinovose, rhamnose, manno-heptulose, sedoheptulose, sucrose, lactose, maltose, cellobiose, galactose, lactose, xylose, arabinose, celloboise, maltose, raffinose, rhamnose, melibiose, ribose, fucose, lyxose, and the like.

An amino sugar or glycosamine is defined as a sugar derivative having an amino group in place of one of the primary or secondary hydroxyls of the sugar. Examples of an amino sugar include but are not limited to glucosamine, galactosamine, mannosamine, and the like.

A sugar alcohol, also known as a polyol, polyhydridic alcohol, or polyalcohol, is a hydrated form of a carbohydrate whose carbonyl group (aldehyde or ketone) has been reduced to a primary or secondary hydroxyl group. Examples of a sugar alcohol include but are not limited to an acyclic polyol such as an alditol or a glycitol, erythritol, sorbitol, mannitol, adonitol, arabitol, zylitol, dulcitol, myo-insoitol, and the like. Further, cyclitols are class of sugar alcohols that are comprised of cycloalkanes containing one hydroxyl group on each of three or more ring atoms.

A deoxysugar is any sugar containing fewer oxygen atoms than carbon atoms, resulting in one or more carbon atoms of the molecule lacking an attached hydroxyl group. See the *American Heritage® Stedman's Medical Dictionary*, 2$^{nd}$ edition, Copyright © 2004 by Houghton Mifflin Company.

Glycosides are acetal derivatives of the cyclic forms of sugars in which the hydrogens of the hemiacetal hydroxyls have been replaced by alkyl or aryl groups, where R is alkyl, aryl, alkylaryl, arylalkyl, substituted alkyl, substituted aryl, substituted alkylaryl, substituted arylalkyl, haloalkyl, alkoxy, aryloxy, heteroaryl, heteroaryloxy, monosaccharide, oligosaccharide, and the like. Examples of an OR replacement group include but are not limited to methoxy, acetoxy, acetyl, phenoxy, or benzyloxy. Preferably, the aglycone component of the glycoside (glycone) may be alkyl or aryl.

An aminoglycoside belongs to a group of antibiotics, which contain a sugar bonded to an amino ($NH_2$) group. Examples include but are not limited to amikacin (Also known as BB-K8), Butirosin A & B, Geneticin, Gentamicin A, Kanamycin A & B (about 5% Kanamycin B), Lividomycin A, Neomycin B & C (about 15% Neomycin C), Paromomycin I & II, 6'-N-Methylamikacin, 4'-Deoxy-6'N-Methylamikacin, Butikacin (Also known as Butakacin), 5''-Amino-5''-Deoxybutirosin A, 1-N-HAPA-Gentamicin B, Gentamicin B, Hybrimycin A1, Hybrimycin A2, Hybrimycin B1, Hybrimycin B2, Kanamycin C, 4,6-di-O-(6-amino-6-deoxy-α-D-glucopyranosyl)-2-deoxystreptamine, 4-O-(6-amino-6-deoxy-.alpha.-D-glucopyranosyl)-6-O-(α-D-glucopyranosyl)-2-deoxystreptamine, 6'-N-methylkanamycin, 6''-Chloro-6''-deoxykanamycin, 6''-Deoxykanamycin A, Kanamycin-6''-uronic acid, Kanamycin-6''-phosphate, 6''-Amino-6''-deoxykanamycin, 6''-Hydrazino-6''-deoxykanamycin, Tetrakis-N-(p-chlorobenzyl)kanamycin, 4'',6''-O-benzylidenekanamycin, 2''-manno-kanamycin, 6''-amino-6''-deoxy-2''-manno-kannamycin, 6''-deoxy-6''-hydrazino-2''-manno-kanamycin, Lividomycin B, Neomycin A (Also known as Neamine), Propikacin (Also known as UK 31214), and the like.

Further examples of an aminoglycoside include but are not limited to Ribostamycin, Ribostamycin-5''-uronic acid, Seldomycin 5, 3-N-Acetylseldomycin 5, 3'-Episeldomycin 5, 6'-N-Methylseldomycin 5, 1-N-HABA-Seldomycin 5, 1-N-Ethylseldomycin 5, Trehalosamine, α-D-mannosyl-α-D-glucosaminide, Apramycin (Also known as Nebramycin), Bluensomycin (Also known as Glebomycin), Gentamicin $C_1$, Gentamicin $C_2$, Gentamicin $C_{1a}$, Gentamicin $C_{2b}$ (Also known as Sagamicin), 3',4'-unsaturated kanamycin B, 3',4'-dideoxy-6'-N-methylkanamycin B, 3'-amino-3'-deoxy-2'-manno-kanamycin, 3'-amino-3'-deoxykanamycin, Netromycin (Also known as netilmicin), 3',4'-dideoxyribostamycin, 3', 4', 5''-trideoxyribostamycin, 3'-Deoxyseldomycin 5, Streptomycin, Dihydrostreptomycin, Dihydrodeoxystreptomycin, Hydroxystreptomycin, N-demethylstreptomycin, Mannosidostreptomycin, Tobramycin (Also known as nebramycin factor 6), Sisomicin, G-52 (Also known as 6'-N-methylisomicin), Verdamicin (Also known as 6'-C-methylsisomicin), Destomycin A, Antibiotic A-396-I, Dibekacin, HABA-dibekacin, HABA-methyldibekacin, Kasugamycin, Fortimicin A, 5-episisomicin, aminocyclitol-aminoglycosides such as 1,3-di-de-N-amidinodihydrostreptomycin. Tylosin, U.S. Pat. No. 3,178,341, Merck Index 9th Ed., No. 9486 is sold commercially as a veterinary antibiotic; spiromycin is disclosed in U.S. Pat. No. 2,943,023, Merck Index 9th Ed., No. 8525; leucomycin is disclosed in Merck Index 9th., No. 5307; magnamycin is disclosed in U.S. Pat. No. 2,960,438 and Merck Index 9th Ed., No. 1812 and oleandomycin is disclosed in U.S. Pat. Nos. 2,757,123 and 2,842,481 and Merck Index 9th Ed., No. 6671.

A nucleoside is a combination of a sugar, either ribose (in RNA) or 2'-deoxyribose (in DNA), with a purine or pyrimidine base. Examples of a nucleoside include but are not limited to adenosine, cytidine, guanosine, uridine, 2'-deoxyadenosine, 2'-deoxyguanosine, 2'-deoxycytidine, 2'-deoxythymidine, and the like.

A derivative of a carbohydrate compound is presented in accordance with the present invention. The carbohydrate compound is selected from a sugar, an amino sugar, a sugar alcohol, an amino glycoside, a deoxysugar, a glycoside, a nucleoside, a substituted sugar, a substituted amino sugar, a substituted deoxysugar, a substituted sugar alcohol, a substituted glycoside, a substituted aminoglycoside, a substituted nucleoside, an aminocyclitol, an aminoglycoside-aminocyclitol, and the like in an embodiment of the present invention.

The derivative further comprises a group of formula I:

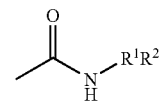

wherein the group is in place of at least one hydrogen atom of at least one hydroxyl group of the aforementioned carbohydrate compounds, or, when present, of at least one amino group of the aforementioned carbohydrate compounds. The substituent $R^1$ is selected from an alkyl group or an azaalkyl group, and $R^2$ is selected from a primary or secondary amino group.

In an embodiment of the present invention, derivatives of the carbohydrate glucosamine having two groups of formula I are presented wherein $R^1$ is $—(CH_2)_3NH(CH_2)_4NH(CH_2)_3—$, $R^2$ is $—NH_2$, and $R^3$ is OH (α and β anomers) (4a); $R^1$ is $—(CH_2)_3NH(CH_2)_4NH(CH_2)_3—$, $R^2$ is $—NH_2$, and $R^3$ is α-$OCH_3$ (4b); $R^1$ is $—(CH_2)_3NH(CH_2)_4NH(CH_2)_3—$, $R^2$ is $—NH_2$, and $R^3$ is α-$OCH_2Ph$ (4c);

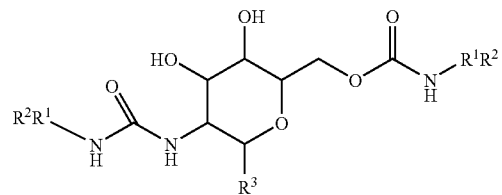

$R^1$ is $—(CH_2)_3NH(CH_2)_4NH(CH_2)_3—$, $R^2$ is $—NH_2$, and $R^3$ is β-$OCH_2Ph$ (4d); and $R^1$ is $—(CH_2)_3NH(CH_2)_4NH(CH_2)_3—$, $R^2$ is $—NH_2$, and $R^3$ is ~OH (4e).

In a second embodiment of the present invention, derivatives of the carbohydrate 2'-deoxyadenosine having the group of formula I are presented wherein $R^1$ is $—CH_2CH_2CH_2NH(CH_2)_4NH(CH)_3—$ and $R^2$ is $—NH_2$ (7); $R^1$ is $—CH_2CH_2CH_2NH(CH_2)_4NH(CH)_3—$ and $R^2$ is $—NH_2$ (9); and $R^1$ is $—CH_2CH_2CH_2NH(CH_2)_4NH(CH)_3—$ and $R^2$ is $—NH_2$ (11).

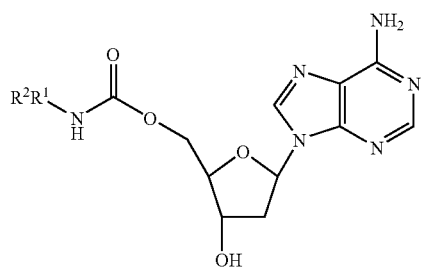

-continued

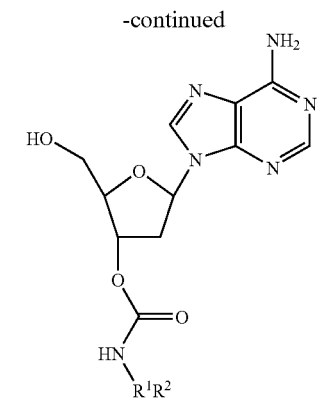

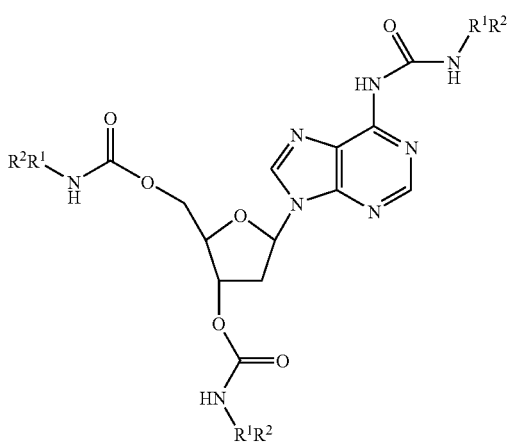

In a third embodiment of the present invention, derivatives of the carbohydrate neomycin having the group of formula I are presented wherein $R^1$ is —CH$_2$CH$_2$— and $R^2$ is —NH$_2$ (14a), and $R^1$ is —CH$_2$CH$_2$NHCH$_2$CH$_2$— and $R^2$ is —NH$_2$ (14b).

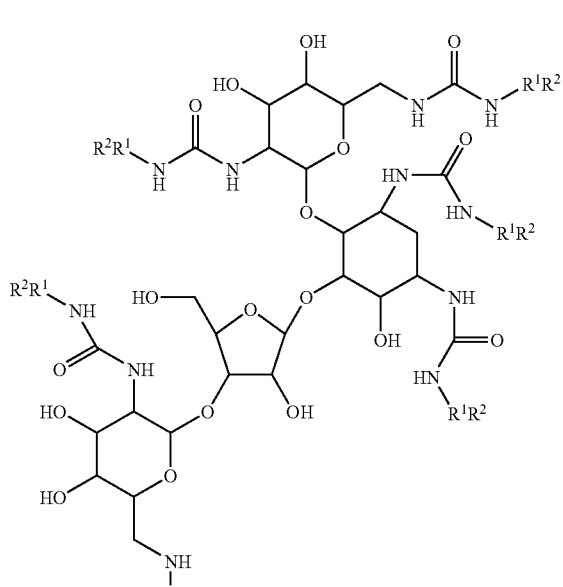

-continued

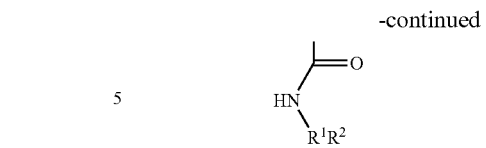

In a fourth embodiment of the present invention, derivatives of the carbohydrate neamine having the group of formula I are presented wherein $R^1$ is —CH$_2$CH$_2$— and $R^2$ is —NH$_2$ (17a), and $R^1$ is —CH$_2$CH$_2$CH$_2$NH(CH$_2$)$_4$NH(CH$_2$)$_3$— and $R^2$ is —NH$_2$ (17b)

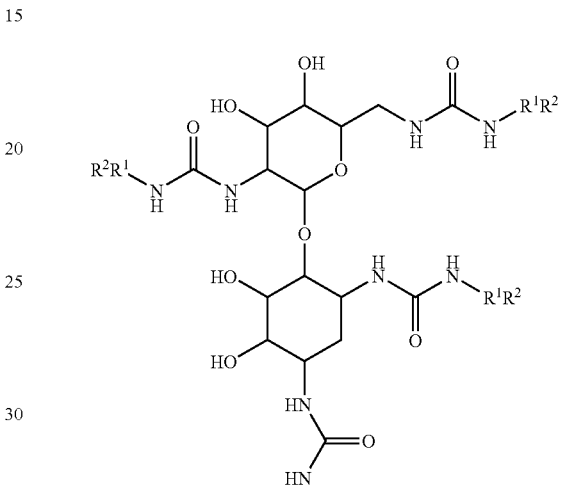

In a fifth embodiment of the present invention, derivatives of the carbohydrate Me-neobiamine having a group of formula I are presented wherein $R^1$ is —CH$_2$CH$_2$ NH(CH$_2$)$_2$— and $R^2$ is —NH$_2$ (20a), and $R^1$ is —CH$_2$CH$_2$CH$_2$ NH(CH$_2$)$_4$NH(CH$_2$)$_3$— and $R^2$ is —NH$_2$ (20b).

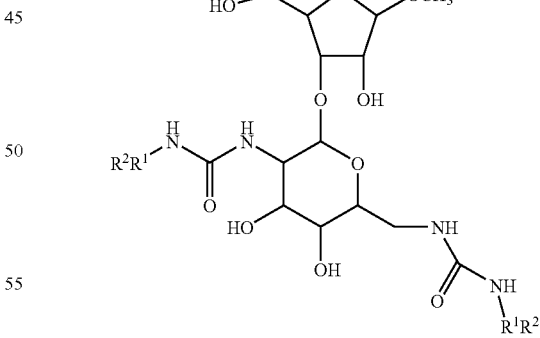

In a sixth embodiment of the present invention, derivatives of the carbohydrate kanamycin having the group of formula I are presented wherein $R^1$ is —CH$_2$CH$_2$—, $R^2$ is —NH$_2$, and $R^3$ is OH (23a); $R^1$ is —CH$_2$CH$_2$NHCH$_2$CH$_2$—, $R^2$ is NH$_2$, and $R^3$ is OH (23b); $R^1$ is —CH$_2$CH$_2$CH$_2$NH(CH$_2$)$_4$NH(CH$_2$)$_3$—, $R^2$ is —NH$_2$, and $R^3$ is —OH (23c); and $R^1$ is —CH$_2$CH$_2$—, $R^2$ is —NH$_2$, and $R^3$ is NH$_2$ (24). The kanamycin derivative (25) is also presented.

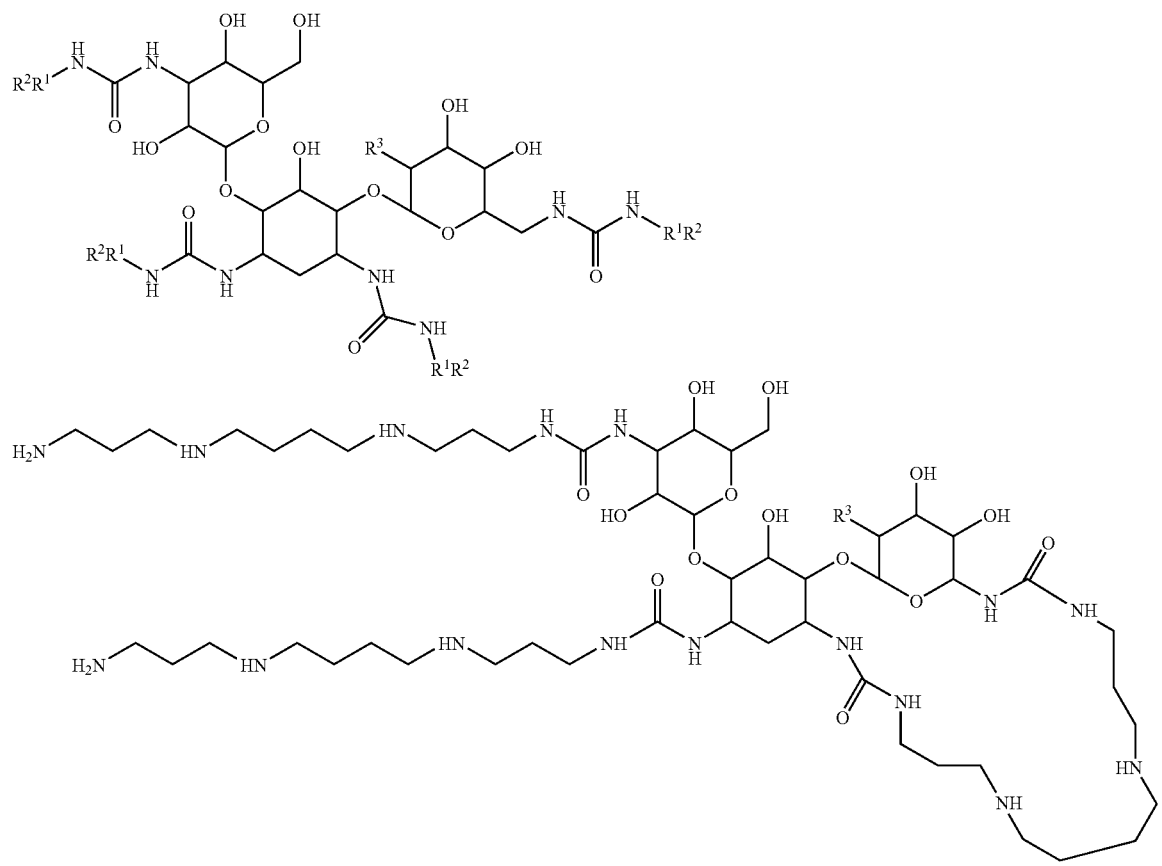

EXPERIMENTAL

The following are examples of the preparation of the aforementioned compounds in accordance with the present invention.

Materials

*Candida antarctica* lipase B (CAL-B, Novozyme 435) was obtained from Novozymes North America, (Franklinton, N.C., USA) as a gift. *Pseudomonas fluorescence* lipase (PFL) was purchased from Amano (Nagoya, Japan). Fast Flow Sepharose SP (FF Sepharose SP), High Performance SP Sepharose (HP Sepharose SP) and Source 15S stationary phase materials were donated by Amersham Pharmacia (Uppsala, Sweden). (note: while the Sepharose materials are agarose based, the Source resins consist of hydrophilized polystyrene divinylbenzene).

The compounds 2'-deoxyadenosine, glucosamine, mannosamine, kanamycin A & B, neomycin sulfate, spermine, calf thymus DNA, chicken egg lysozyme, horse heart cytochrome-C, ammonium bicarbonate, sodium phosphate (dibasic), and sodium phosphate (monobasic) were purchased from Sigma (Saint Louis, Mo.). Ethylenediamine, diethylenetriamine, vinyl chloroformate and dry THF were purchased from Aldrich (Milwaukee Wis.). Acetone-O-(vinyloxy)carbonyl)oxime was prepared according to literature protocol, Garcia-Alles, L. F.; Magdalena, J.; Gotor, V.; *J. Org. Chem.* 1996, 61, 6980-6986, which is incorporated by reference herein.

The glucosamine analogs (compounds 1b-1e) neamine (compound 5) and methyl neobiosamine (compound 8) were prepared according to literature procedures: Shafizadeh, F.; Meshreki, M. H.; R. A. Susott; *J. Org. Chem.* 1973, 38, 1190-1194; Gross, P. H., Jeanloz, R. W., *J. Org. Chem.* 1967, 32, 2759-2763; and Rinehart, K. L., Argoudelis, A. D.; Goss, W. A., Sohler, A., Schaffner, C. P. *J. Am. Chem. Soc.* 1996, 82, 3938-3946, all of which are incorporated by reference herein.

$^1$H and $^{13}$C NMR spectra were recorded on a Varian spectrometer with TMS as the internal standard. Chemical shifts are reported in ppm and the coupling constants (J) are given in Hertz (Hz). ESI-MS and MALDI-TOF were measured on a Varian mass spectrometer. Flash chromatography was performed on 60-200 mesh silica gel (Sigma MO). Product yields, purities and spectroscopic data is provided in the supporting information section. Cation-exchange chromatography was performed on Fast Flow Sepharose SP (FF Sepharose SP) using ammonium bicarbonate ($NH_4HCO_3$) as a mobile phase. Fluorescence and absorbance analyses were carried out using a Perkin Elmer plate reader and the results were analyzed using the software HTSoft 2.0.

Procedures

I. Generation of Glucosamine and Mannosamine Derivatives.

Scheme 1 depicts a chemoenzymatic synthesis of glucosamine-based and mannosamine-based derivatives in accordance with the present invention. Referring to Scheme 1, the synthesis of vinyl carbamate linkers, 2a-2e, is presented in an embodiment of the present invention. Vinyl chloroformate (426 µl, 5.0 mmol) was added drop-wise to a phosphate buffer solution (40 ml, pH 8.0, 50 mM) of compounds (1a-1e)

(2.0 mmol) for 1 h at 0° C. The reaction mixture was vigorously stirred and the solution was maintained at pH 8.0 by continuously adding 1.0 N NaOH. After 5 h, compounds 2c and 2d were directly precipitated from the buffer solution and then washed by distilled $H_2O$ and dried under vacuum with >95% purity. For the other compounds, the reaction mixture was lyophilized for 24 h to afford crude product, which was purified by silica gel flash chromatography using EtOAc/MeOH (5:1 and 2:1). The above procedure resulted in moderate to good yields of 2a, 88%; 2b, 33%; 2c, 42%; 2d, 67%; 2e, 80%.

Lipase-catalyzed regioselective synthesis of 6-vinylcarbonate linkers, 3a-3e, is presented in an embodiment of the present invention. Compounds 2a-2e (0.6 mmol), acetone O-(vinyloxy)carbonyl)oxime (1.8 mmol), and *Candida antarctica* lipase B (CAL) in 15 ml of dry THF were shaken at 200 rpm at 45° C. for 24-96 hr. The reaction was monitored by TLC. After evaporation of the solvent, the residue was purified by flash chromatography using hexane/EtOAc (2:1, 1:2) to afford 3a-3e. The yields were 3a, 91%; 3b, 73%; 3c, 83%; 3d, 48%; 3e, 82%. The 6-vinyloxy derivatives were the sole products in most cases.

Generation of spermine derivatives of glucosamine and mannosamine, 4a-4e, is presented in an embodiment of the present invention. A solution of the vinyloxy linkers, 3a-3e, (0.2~0.4 mmol) and spermine (3 equiv relative to free amine group) in ethanol (10 ml) was shaken at 45° C. and 250 rpm for 96 h. After removal of ethanol under pressure, the residue was neutralized with 1.0 N HCl at 0° C. After lyophilization the powder was purified using cation-exchange chromatography (resin: FF Sepharose SP, eluent: 0.1-0.5 M $NH_4HCO_3$ solution) as described infra. The fraction collection was monitored by TLC and detected by ninhydrin reagent solution after heating at 100° C.

The $NH_4HCO_3$ solution was removed by lyophilization to yield the desired products (4a-4e) with purities ranging from 85~95% based on NMR and MS analyses and isolated yields ranging from 10%~25% after cation-exchange chromatography. It was observed that the formation of isomers was usually lower than 20~40%, presumably due to stronger steric effects of secondary amino than the primary amino groups in spermine. The mannosamine-spermine derivative (4e) was synthesized in a similar manner with a 23% overall yield.

Scheme 1

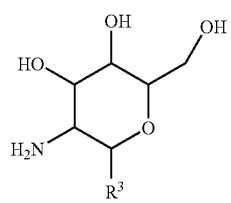

1a $R^3$ = OH (alpha & beta anomers)
1b $R^3$ = alpha ——$OCH_3$
1c $R^3$ = alpha ——$OCH_2PH$
1d $R^3$ = beta ——$OCH_2PH$ vinyl chloroformate
pH 8.0, 0° C., 5 h -continued

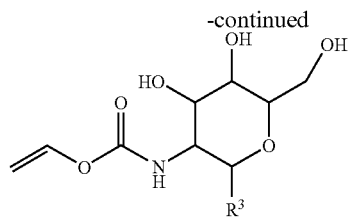

2a $R^3$ = OH (alpha & beta anomers)
2b $R^3$ = alpha ——$OCH_3$
2c $R^3$ = alpha ——$OCH_2PH$
2d $R^3$ = beta ——$OCH_2PH$ CAL—B, THF
30° C., 48 h

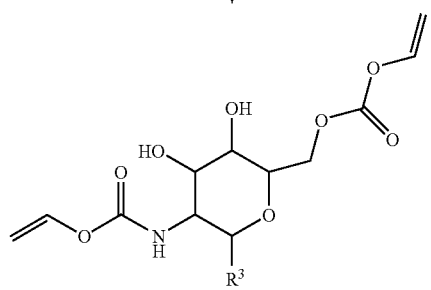

3a $R^3$ = OH (alpha & beta anomers)
3b $R^3$ = alpha ——$OCH_3$
3c $R^3$ = alpha ——$OCH_2PH$
3d $R^3$ = beta ——$OCH_2PH$ spermine
ethanol, 45° C.
96 h

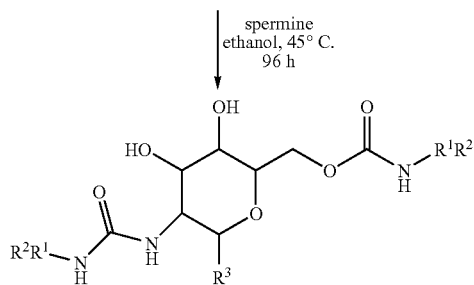

4a $R^1$ = ——$(CH_2)_3NH(CH_2)_4NH(CH_2)_3$——,
  $R^2$ = ——$NH_2$, $R^3$ = OH (alpha & beta anomers)
4b $R^1$ = ——$(CH_2)_3NH(CH_2)_4NH(CH_2)_3$——,
  $R^2$ = ——$NH_2$, $R^3$ = alpha ——$OCH_3$
4c $R^1$ = ——$(CH_2)_3NH(CH_2)_4NH(CH_2)_3$——,
  $R^2$ = ——$NH_2$, $R^3$ = alpha ——$OCH_2PH$
4d $R^1$ = ——$(CH_2)_3NH(CH_2)_4NH(CH_2)_3$——,
  $R^2$ = ——$NH_2$, $R^3$ = beta ——$OCH_2PH$ II. Generation of 2'-deoxyadenosine Derivatives Scheme 2 depicts a chemoenzymatic synthesis of a 2'-deoxyadenosine derivative containing a spermine chain at the 6'-hydroxyl group and a 2'-deoxyadenosine derivative containing a spermine on the 3'-hydroxyl group in accordance with the present invention. Referring to scheme 2, the synthesis of monospermine derivatives of 2'-deoxyadenosine, 7 and 9, is presented in an embodiment of the present invention.

The vinyl linker 6, was readily formed using CAL-B catalyzed acylation with high yields (87%) per liter according to literature protocol, Rinehart, K. L.; Argoudelis, A. D.; goss, W. A.; Sohler, A.; Schaffner, C. P. *J. Am. Chem. Soc.* 1996, 82, 3938-3946 which is incorporated by reference herein. Aminolysis with excess spermine gave the desired product, 7. A solution of the vinyloxy derivative 6 (0.3 mmol) and spermine (0.9 mmol) in THF (20 ml) was shaken at 30° C. and 250 rpm for 24 h. After removal of THF the residue was purified by silica gel flash chromatography using MeOH/1.0 M NaCl (10:1) to yield the pure product 7 (69% yield after flash chromatography).

*Pseudomonas fluorescence* lipase (PFL) was used to catalyze the acylation of 2'-deoxyadenosine. The vinyl carbonate linker was introduced at 3'-hydroxyl as described above, with high regioselectivity (>10:1, 3'-OH versus 6'-OH group) to yield the intermediate product, 8 in reasonable yield (28%) according to literature protocol, Rinehart, K. L.; Argoudelis, A. D.; goss, W. A.; Sohler, A.; Schaffner, C. P. *J. Am. Chem. Soc.* 1996, 82, 3938-3946 which is incorporated by reference herein. The desired monospermine derivative, 9 was obtained upon aminolysis with sper mine (50% yield, 95% purity).

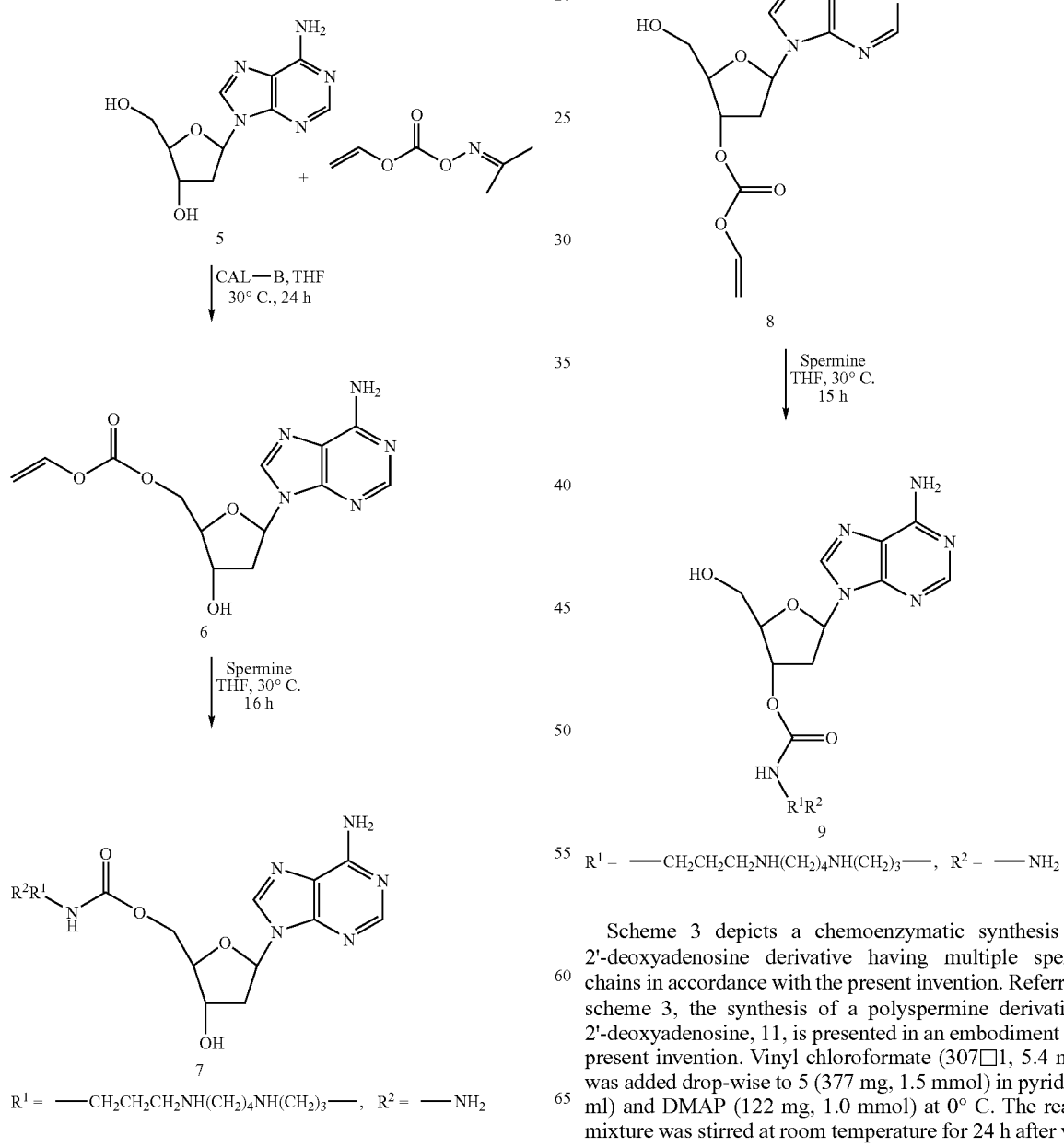

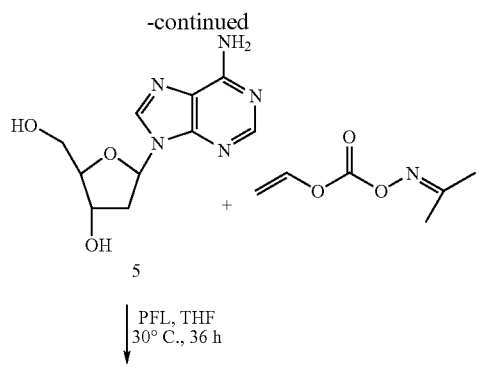

Scheme 3 depicts a chemoenzymatic synthesis of a 2'-deoxyadenosine derivative having multiple spermine chains in accordance with the present invention. Referring to scheme 3, the synthesis of a polyspermine derivative of 2'-deoxyadenosine, 11, is presented in an embodiment of the present invention. Vinyl chloroformate (307□l, 5.4 mmol) was added drop-wise to 5 (377 mg, 1.5 mmol) in pyridine (5 ml) and DMAP (122 mg, 1.0 mmol) at 0° C. The reaction mixture was stirred at room temperature for 24 h after which the reaction mixture was diluted with EtOAc (20 ml) and the mixture was washed with 1.0 N HCl, saturated NaHCO$_3$, followed by saturated NaCl.

The organic phase was dried over MgSO$_4$. After evaporation of solvent the residue was purified by flash chromatography (hexane/EtOAc, 1:1 and 1:5) to afford the product 10 (yield, 28%). The polypermine derivative, 11 (yield 32%, purity, 85%), was synthesized in a manner similar to that described in the procedure above for the generation of spermine derivatives of glucosamine and mannosamine, 4a-4e.

III. Generation of Polyamine Derivatives of Neomycin, Neamine, and Methyl-Neobiosamine Scheme 4 depicts a synthesis of derivatives of neomycin 12, neamine 15, and methyl-neobiosamine 18 in accordance with the present invention. Referring to Scheme 4, the synthesis of a spermine derivative of neomycin is presented in an embodiment of the present invention. The vinyl carbamate linkers of neomycin, neamine and methyl-neobiosamine (13, 16, 19) were synthesized as described for the synthesis of the vinyl carbamate linkers 2a-2e in moderate to good yields (13, 71%; 16, 66%; 19, 48%, respectively).

A solution of vinyloxy linkers 13 and 16, (0.2~0.4 mmol) and ethylenediamine (2 ml) were shaken at 35° C. and 250 rpm for 24-48 h. The excess ethylenediamine was evaporated under pressure and the residue was precipitated by MeOH/EtOAC and then washed with EtOAc to yield pure products: 14a and 17a respectively.

A solution of vinyloxy linkers 13 and 19 (0.3 mmol) and diethylenetriamine (4 equiv relative to free amine group) in ethanol (10 ml) was shaken at 45° C. and 250 rpm for 96 h. After removal of ethanol under vacuum, the residue was precipitated and washed as described in procedure 4 to afford 14b and 20a respectively.

The spermine derivatives of neamine and methyl-neobiosamine, 17b and 20b, respectively were synthesized according to the procedure for the generation of spermine derivatives of glucosamine and mannosamine above and were obtained in moderate to good yields.

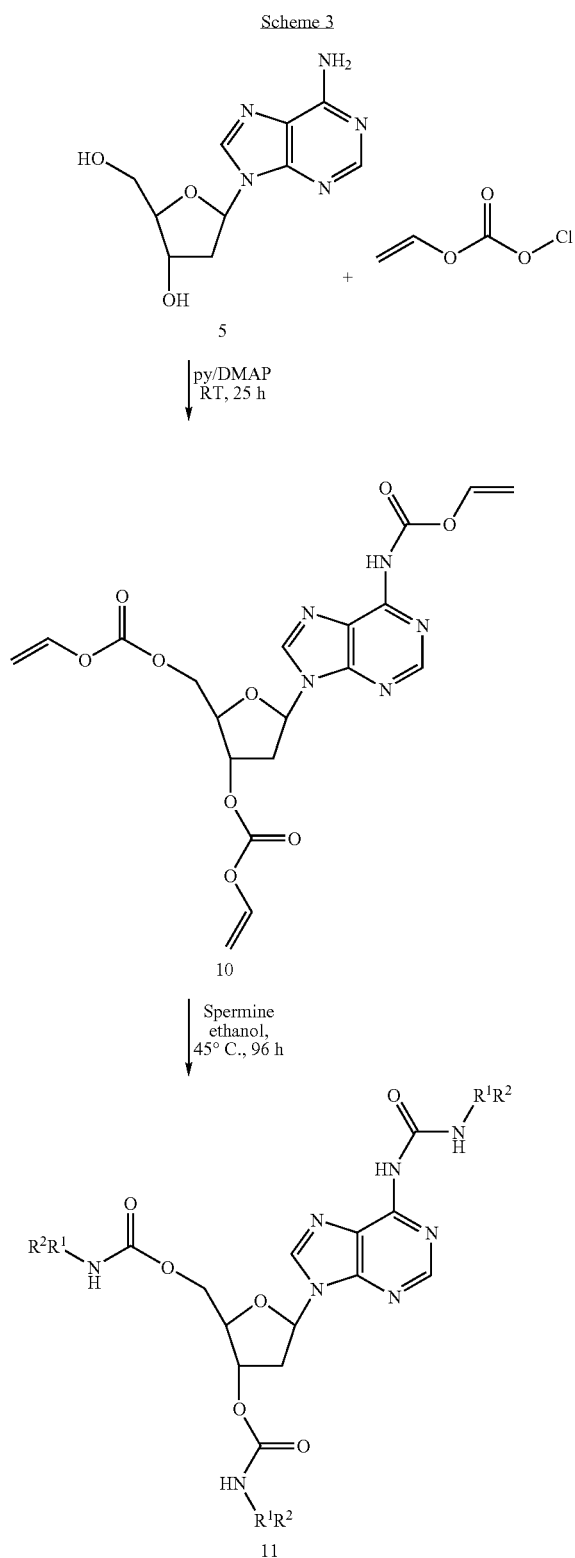

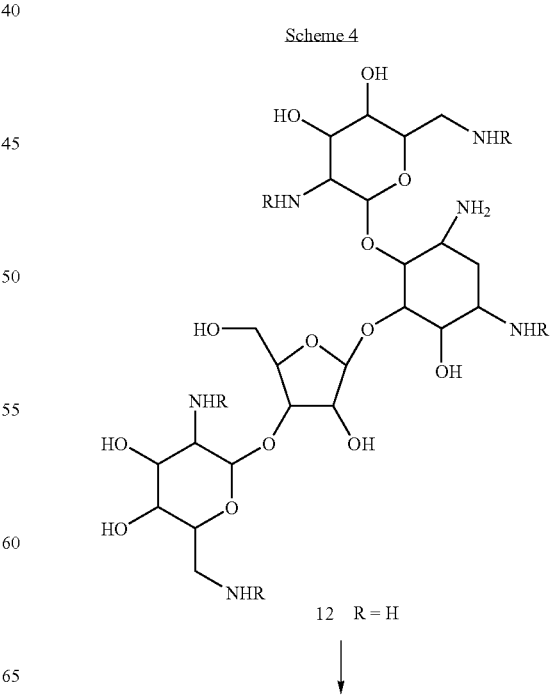

-continued
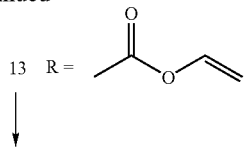
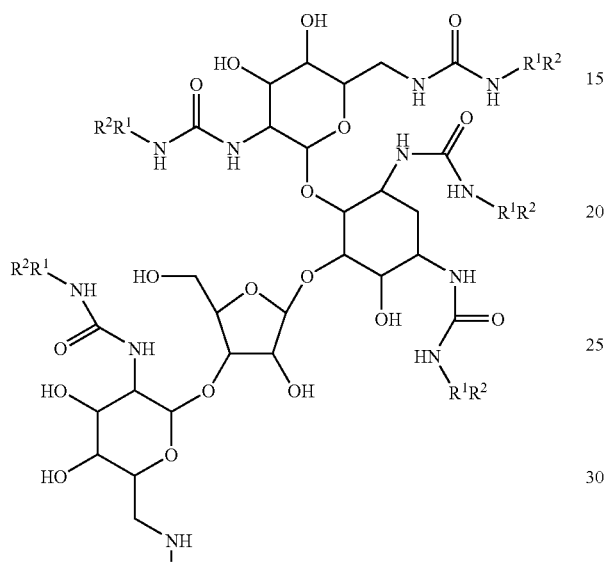
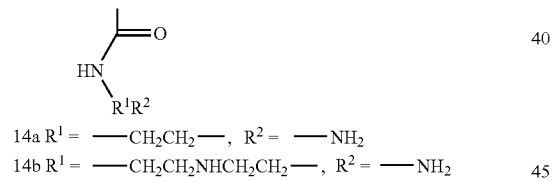
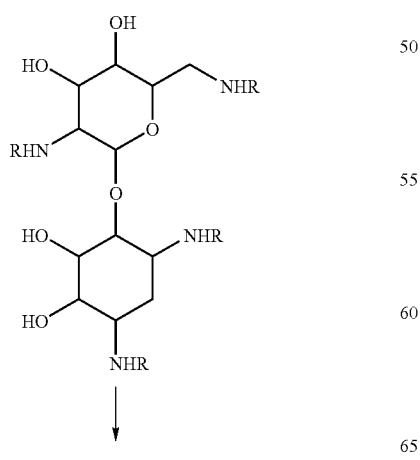
-continued
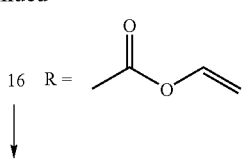
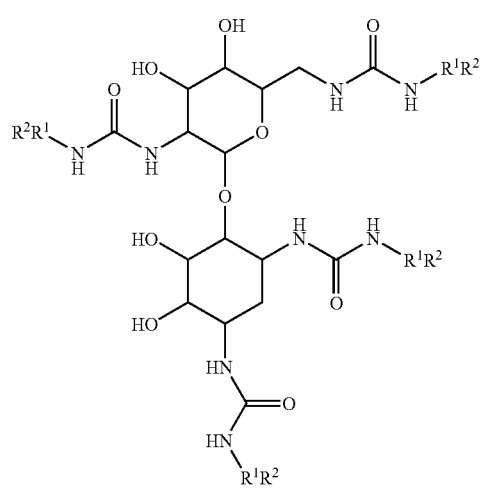
17a R¹ = —CH₂CH₂—, R² = —NH₂
17b R¹ = —CH₂CH₂CH₂NH(CH₂)₄NH(CH₂)₃—, R² = —NH₂
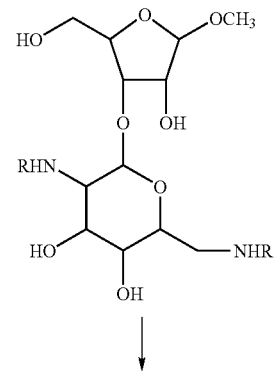
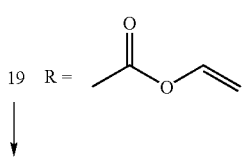

-continued

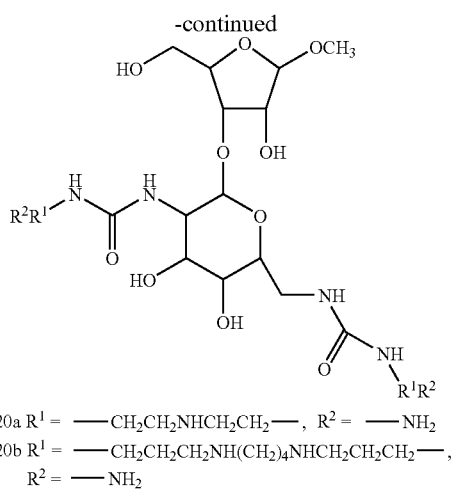

20a $R^1 = $ —CH$_2$CH$_2$NHCH$_2$CH$_2$—, $R^2 = $ —NH$_2$
20b $R^1 = $ —CH$_2$CH$_2$CH$_2$NH(CH$_2$)$_4$NHCH$_2$CH$_2$CH$_2$—,
$R^2 = $ —NH$_2$

IV. Generation of Polyamine Derivatives of Kanamycin

Scheme 5 depicts a generation of polyamine derivatives of kanamycin in accordance with the present invention. Referring to scheme 5, the synthesis of vinyl carbamate linkers (22a and 22b) is presented in an embodiment of the present invention. The carbamate linkers for kanamycin A and B were synthesized according to the procedure for the generation of spermine derivatives of glucosamine and mannosamine above and were obtained in moderate to good yields; 22a, yield 37%, 22b, yield 84%.

The derivatives 22a or 22b (0.2–0.4 mmol), and ethylenediamine (2 ml) were shaken at 35° C. and 250 rpm for 24-48 h. The excess ethylenediamine was evaporated under pressure and the residue was precipitated by MeOH/EtOAC and then washed with EtOAc to yield pure products 23a and 24, respectively.

A solution of 22a (0.3 mmol) and diethylenetriamine (4 equiv relative to free amine group) in ethanol (10 ml) was shaken at 45° C. and 250 rpm for 96 h. After removal of ethanol in vacuo the residue was precipitated and washed as procedure A to afford 23b (yield, 76%).

The spermine derivatives 23c and 25 (structure deduction based on ESI-MS, $^1$H and $^{13}$C NMR data), were synthesized according to the procedure for the generation of spermine derivatives of glucosamine and mannosamine above and were obtained in moderate to good yields (7% and 27% respectively) with purities >95% after cation exchange chromatography.

Scheme 5

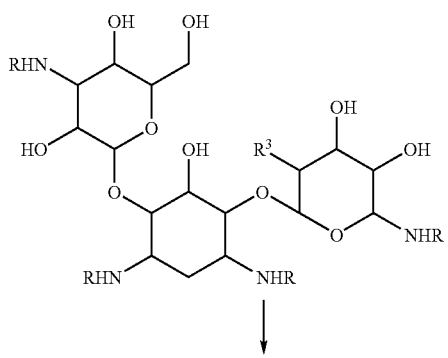

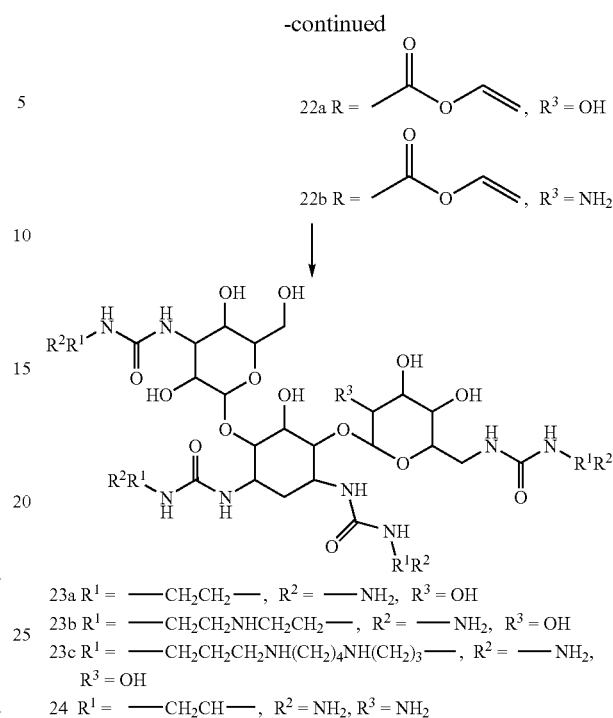

22a R = ![carbamate structure], $R^3 = $ OH

22b R = ![carbamate structure], $R^3 = $ NH$_2$

23a $R^1 = $ —CH$_2$CH$_2$—, $R^2 = $ —NH$_2$, $R^3 = $ OH
23b $R^1 = $ —CH$_2$CH$_2$NHCH$_2$CH$_2$—, $R^2 = $ —NH$_2$, $R^3 = $ OH
23c $R^1 = $ —CH$_2$CH$_2$CH$_2$NH(CH$_2$)$_4$NH(CH$_2$)$_3$—, $R^2 = $ —NH$_2$, $R^3 = $ OH
24 $R^1 = $ —CH$_2$CH—, $R^2 = $ NH$_2$, $R^3 = $ NH$_2$

A method for separating one or more components of a biomolecule mixture is presented in accordance with the present invention. The means of separation is an ion exchange chromatographic system operated in a displacement mode. The displacement mode comprises sequentially perfusing the chromatographic system with a first solution comprising the biomolecule mixture and a second solution comprising a derivative of a carbohydrate compound.

The derivative of the carbohydrate compound is chosen from any of the aforementioned carbohydrate derivatives described supra in an embodiment of the present invention. The biomolecule mixture may include but is not limited to mixtures of proteins, including gylcosylated proteins, peptides, nucleotides, nucleosides, oligonucleotides, sphingolipids, phospholipids, and the like.

A modified batch displacement assay was used to investigate displacer efficacy of the carbohydrate derivatives over a wide range of concentrations. The carbohydrate derivatives from hereon will be referred to as the displacer candidates unless otherwise specified. Different input concentrations of the displacer candidates were employed to determine the $DC_{50}$ value, which is the input displacer concentration required to displace fifty percent of the initially bound protein. The lower the $DC_{50}$ value the more efficacious is the displacer candidate.

FIG. 1 depicts a graph for the displacement of cytochrome-C by various input concentrations of neamine and its derivatives on HP Sepharose SP in accordance with the present invention. Referring to FIG. 1, the Y axis is % cytochrome-C displaced and the X axis is input displacer concentration in mmol. The curves 103, 104, and 105 are neamine, 17a, and 17b respectively. The resulting plots were then employed to determine the $DC_{50}$ values of neamine ($DC_{50}$, 5.6 mM), 17a ($DC_{50}$, 2.1 mM) and 17b ($DC_{50}$, 0.7 mM).

Table 1 is of displacer candidates and their respective $DC_{50}$ values of horse cytochrome-C on HP Sepharose SP and Source 15S cation exchange resins in accordance with the present invention. Column 201 is the displacer candidate evaluated. Column 202 is $DC_{50}$ values of horse cytochrome-C on HP Sepharose SP. Column 203 is the $DC_{50}$ values of horse cytochrome-C on Source 15S cation exchange resin. The above approach was employed to determine the $DC_{50}$ values of the displacer candidates for the displacement of horse cytochrome-C on HP Sepharose SP and Source 15S cation exchange resins at pH 6.0.

TABLE 1

| Displacer | $DC_{50}$-Cytochrome C on HP Sepharose SP (mM) | $DC_{50}$-Cytochrome C on Source 15S (mM) |
|---|---|---|
| 17b | 0.7 ± na | 0.6 ± 0.03 |
| 23c | 1.0 ± na | 0.9 ± 0.08 |
| 25 | 1.0 ± 0.02 | 2.4 ± 0.13 |
| 14b | 1.1 ± 0.06 | 0.9 ± 0.12 |
| 20b | 1.1 ± na | 0.8 ± 0.04 |
| 4c | 1.3 ± 0.08 | 0.8 ± 0.02 |
| 14a | 1.6 ± 0.01 | 1.3 ± 0.09 |
| 24 | 1.9 ± 0.01 | 1.9 ± 0.06 |
| 23a | 2.0 ± 0.15 | 1.7 ± 0.02 |
| 17a | 2.1 ± 0.06 | 2.3 ± 0.04 |
| 11 | 2.3 ± na | 1.1 ± 0.14 |
| 4e | 2.7 ± 0.68 | 1.1 ± 0.00 |
| 4a | 2.8 ± na | 0.9 ± 0.07 |
| 4d | 2.8 ± 0.20 | 0.8 ± 0.00 |
| Neomycin | 2.8 ± 0.87 | 1.7 ± 0.02 |
| 4b | 3.6 ± 0.25 | 0.8 ± 0.04 |
| 23b | 4.1 ± 0.29 | 2.4 ± 0.13 |
| Spermine | 4.8 ± 1.04 | 4.3 ± 0.64 |
| Neamine | 5.6 ± 1.99 | 4.9 ± 1.67 |
| Bekanamycin | 6.2 ± 0.37 | 3.1 ± 2.29 |
| Spermidine | 7.7 ± 1.44 | 5.8 ± 0.44 |
| 20a | 9.4 ± 2.65 | 4.8 ± 0.03 |
| Diethylenetriamine | 10.8 ± 0.19 | 14.4 ± 3.67 |
| 7 | 11.7 ± 0.10 | 6.2 ± 0.46 |
| 9 | 12.3 ± 0.25 | 12.9 ± 1.46 |
| Ethylenediamine | 20.2 ± 2.67 | 17.6 ± 2.15 |

Referring to Table 1, while commercially available displacers such as spermine and neomycin show moderate to high affinities as displacers with $DC_{50}$ values of 4.8 and 2.8 mM, respectively; compounds 17b (neamine tetraspermine) and 23c (kanamycin A tetraspermine) showed sub-millimolar $DC_{50}$ values. Furthermore, eleven displacers exhibited higher affinities than neomycin while the others had comparable affinities. These results are important in that they demonstrate that individual displacers with moderate affinities can be conjugated to generate a new class of high affinity displacers. This represents a novel approach for the design of high affinity displacers for biomolecule purification by displacement chromatography.

The $DC_{50}$ values of neomycin and its derivatives 14a (neomycin derivatized with ethylenediamine) and 14b (neomycin derivatized with diethylenetriamine) were 2.8, 1.6 and 1.1 mM, respectively for the displacement on HP Sepharose SP. This indicates that displacer affinity increases as larger polyamine homologues are conjugated to neomycin. Neomycin derivatized with diethylenetriamine 14a was found to have the highest affinity among the neomycin derivatives. It turns out that the displacer affinity for the molecules as well as their derivatives followed the trend neomycin>neamine>neobiosamine.

Glucosamine and mannosamine derivatives 4a-4e showed interesting trends in their $DC_{50}$ values on HP Sepharose SP. The $DC_{50}$ values of 4a, 4d and 4e are similar (~2.7-2.8 mM). However, 4c and 4b show very different affinities. While 4c ($DC_{50}$=1.3 mM) has the highest affinity among this family of compounds, 4b ($DC_{50}$=3.6 mM) has the lowest affinity.

The influence of the stationary phase on displacer affinity was investigated using a second strong cation exchange resin, Source 15S. The performance of the displacer candidates on Source 15S is significantly different from that observed on HP Sepharose SP, with as many as eight displacers exhibiting sub-millimolar affinities. Although neamine-tetraspermine (17b) and kanamycin A-tetraspermine (23c) were still among the highest affinity displacers with $DC_{50}$ values of 0.6 and 0.9 mM, respectively; other displacers including 4b, 4c, 4d, 4a, 14b and 20b had comparable sub-millimolar affinities.

The affinities of the glucosamine/mannosamine derivatives (4a-4e) on the Source 15S resin showed significant differences when compared to their affinities on HP Sepharose SP. The $DC_{50}$ values of these molecules ranged between 0.8 to 1.1 mM for the Source resin indicating that these were among the highest affinity molecules on that resin. The glucosamine/mannosamine-derivatives (4a-4e) follow the affinity trend 4b-4c-4d>4a>4e ($DC_{50}$ values: 0.8, 0.8, 0.8, 0.9 and 1.1 mM respectively). It is also interesting to note that 4b ($DC_{50}$, 3.6 mM), the least effective displacer among this family of molecules on the HP Sepharose SP resin, was the most effective on the Source resin ($DC_{50}$, 0.8 mM). The trend described above indicates that displacer efficacy on the Source resin increased with the introduction of hydrophobic/aromatic moieties in the molecule. These results indicate that although the displacer candidates were designed for generic high affinity displacers, unique selectivities can be observed on different resins.

Figure 2:
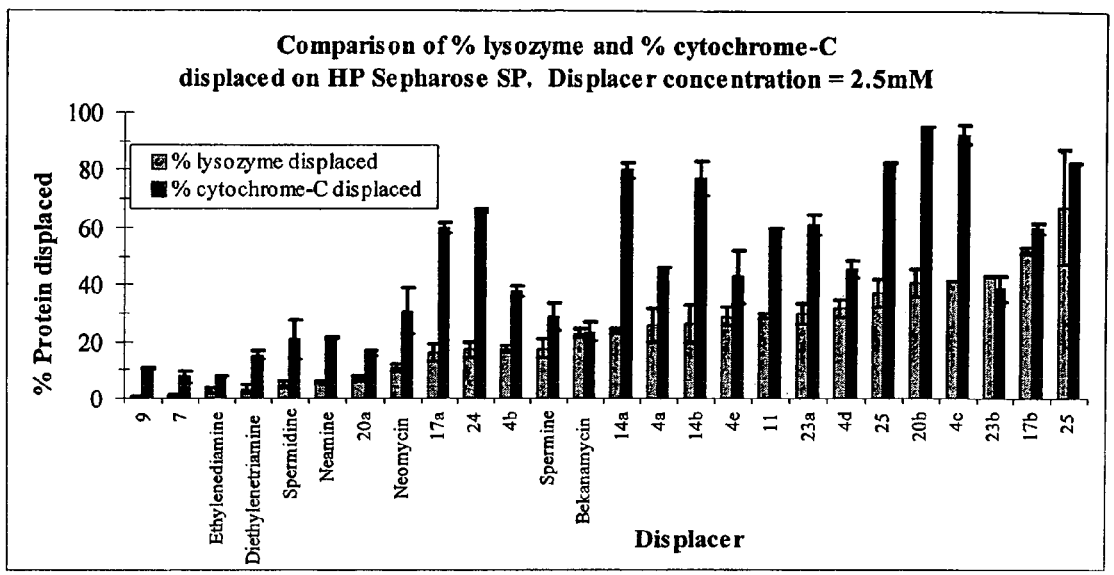
FIG. 2 depicts a graph comparing the % lysozyme and % cytochrome-C displaced on HP Sepharose SP, in accordance with the present invention.

FIG. 2 depicts a graph comparing the % lysozyme and % cytochrome-C displaced on HP Sepharose SP in accordance with the present invention. The Y axis is % protein displaced. The X axi is the displacer candidate evaluated. The displacer candidate concentration is 2.5 mM in an embodiment of the present invention. In order to evaluate the displacer candidates with another protein, experiments were carried out with chicken-egg lysozyme adsorbed on HP Sepharose SP.

Referring to FIG. 2, a comparison of the percent protein displaced for both lysozyme and cytochrome-C at displacer concentrations of 2.5 mM is shown. The data is arranged in increasing order of percent lysozyme displaced. A large number of the displacer candidates had significantly higher affinities than those of the previously identified commercial compounds neomycin and spermine. In addition, molecules such as kanamycin A tetraspermine (23b) and neamine tetraspermine (17b) were found to be particularly effective at displacing lysozyme with values of 67.8 and 52.8 percent protein displaced, respectively.

As seen from these screening results, the rational design of displacer candidates has resulted in the identification of several novel high affinity displacers for cation exchange systems. These molecules have the potential to significantly improve the efficiency of ion exchange processes ranging from large scale preparative chromatography to microscale proteomic applications.

Experimental

The following is an example of the procedure for separating one or more components of a biomolecule mixture by the means of an ion exchange chromatographic system in accordance with the present invention.

Purification of the Aminoglycoside-Polymamine Displacer Candidates

The aminoglycoside-polyamine compounds were purified prior to use as follows. In the case of ethylenediamine, the desired aminoglycoside polyamines were produced in a high yield and good purity after the evaporation of excess ethylenediamine in vacuo and simple precipitation with a mixture of ethyl acetate and methanol (for example, 14a and 17a, >99% yield, >95% purity).

For the purification of diethylenetriamine and spermine derivatives, a parallel batch screen using resin packed in a membrane-bottomed 96-well microtiter plate was used to identify the right resin-mobile phase combination for the subsequent chromatography steps. Cation-exchange chromatography using Fast Flow Sulfopropyl Sepharose (FF Sepharose SP) with a multi-step gradient of ammonium bicarbonate were identified as the best candidates for the stationary phase and the mobile phase conditions respectively (screening data not shown). The fact that ammonium bicarbonate could be removed from the final product by freeze-drying was also a significant factor in its selection as the mobile phase.

Protein Adsorption

The bulk stationary phase (HP Sepharose SP or Source 15S) was first washed once with de-ionized water and then three times with the buffer, (50 mM phosphate, pH 6.0) and allowed to equilibrate for 2 hours. After gravity-settling of the stationary phase, the supernatant was removed and 3.0 mL of the remaining stationary phase slurry was equilibrated with 36 ml containing 3 mg/ml of the protein (horse heart cytochrome-C or chicken egg lysozyme) in 50 mM phosphate buffer, pH 6.0, at 20° C.

The protein was equilibrated with the resin for five hours in order to attain complete equilibration during which, the stationary phase was allowed to gravity-settle. Upon settling, the supernatant was removed and the protein content in the supernatant was determined using absorbance detection at 280 or 405 nm using a plate reader. The mass of the protein adsorbed on the stationary phase was determined by mass balance.

Determination of $DC_{50}$

For the screening experiments, 300 μL of different initial concentrations (ranging from 0.3 to 5 mM) of a displacer solution was added to 25 μL aliquots of the stationary phase slurry with bound protein. (note: a different displacer candidate and concentration were employed for each vial to enable parallel screening). The system was equilibrated for 5 h. After equilibrium was achieved, the supernatant was removed and the protein content was determined by absorbance detection at 280 or 405 nm using a plate reader.

The percent protein displaced, was calculated for each aliquot based on the protein mass balance and the data was plotted as a function of the initial displacer concentration. The resulting plots were then employed to determine the initial displacer concentration required to displace fifty percent of the adsorbed protein (i.e. the $DC_{50}$).

Figure 3:
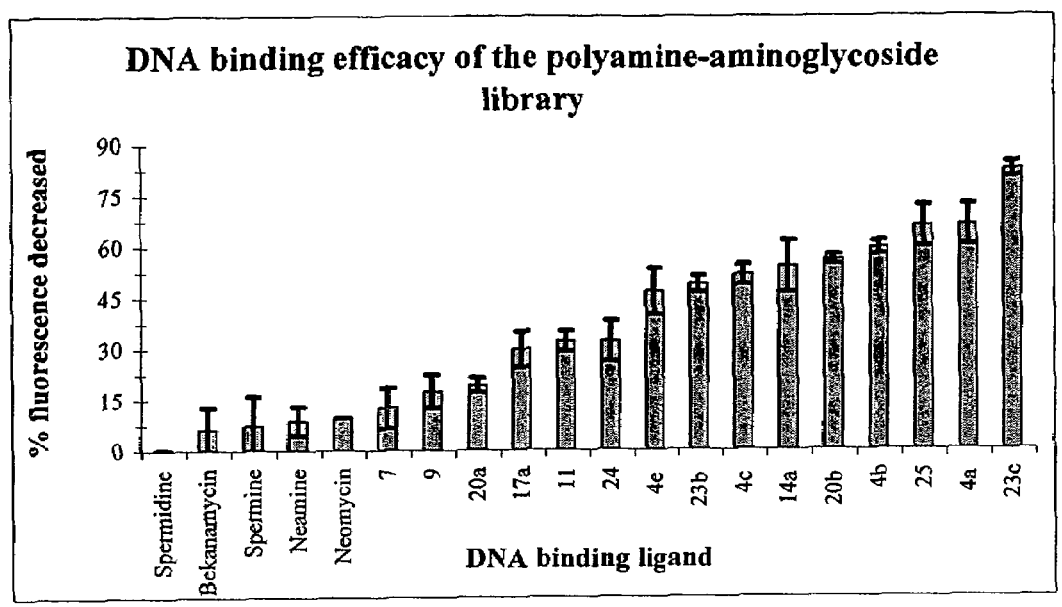
FIG. 3 depicts a graph of DNA binding efficacy of the displacer candidates, in an embodiment of the present invention.

A method for condensing DNA comprising combining the DNA with at least one of the aforementioned derivatives of a carbohydrate compound wherein the DNA is bound to the carbohydrate compound is presented in accordance with the present invention. FIG. 3 depicts a graph of DNA binding efficacy of the displacer candidates in an embodiment of the present invention. The Y axis is % fluorescence decreased and the X axis is the carbohydrate derivative evaluated.

Referring to FIG. 3, an ethidium bromide displacement assay was employed to evaluate the DNA-binding affinity of carbohydrate derivatives in a 96-well format. Using this screen, the percent fluorescence decreased was used as a parameter to rank the DNA-binding efficacy of the various compounds.

Commercially available polyamines such as spermidine, spermine, bekanamycin and neomycin showed relatively low efficacies. On the other hand, a large number of the carbohydrate derivatives acted as effective DNA binding agents. Particularly significant are the results with 23c (kanamycin A-tetraspermine), 4a, 25 and 4b, all of which resulted in greater than 60% fluorescence decreased. This data demonstrates that the aminoglycoside polyamine displacers exhibit high DNA-binding efficacies.

COLUMN 17
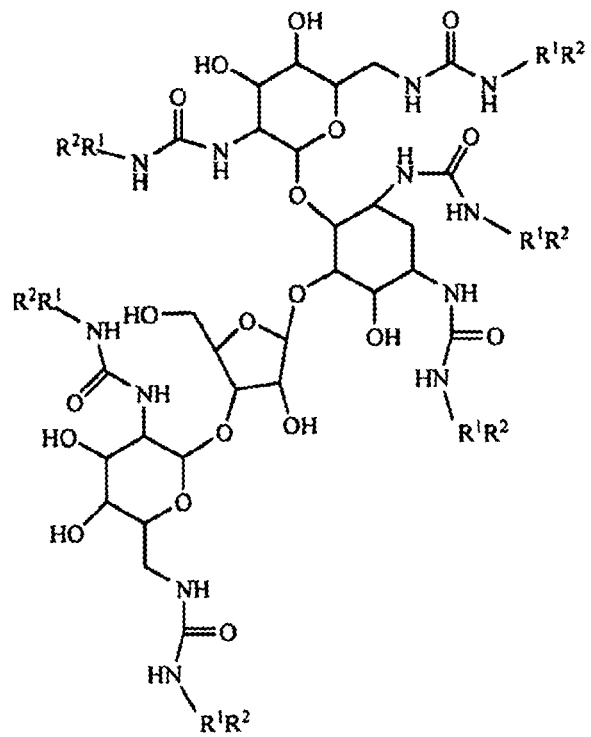

COLUMN 24-25
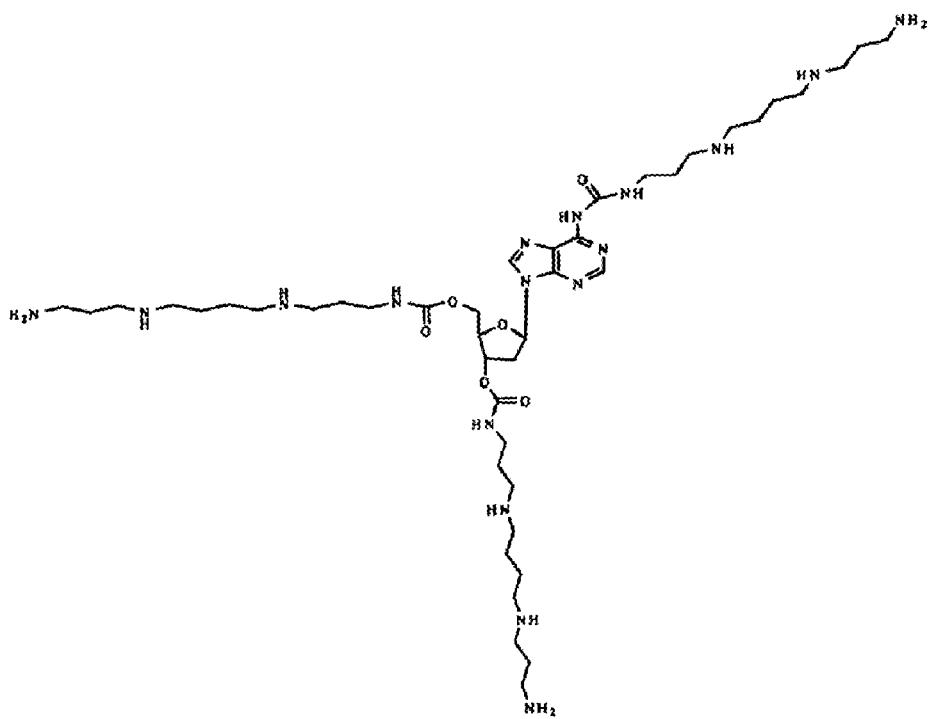

COLUMN 25-26
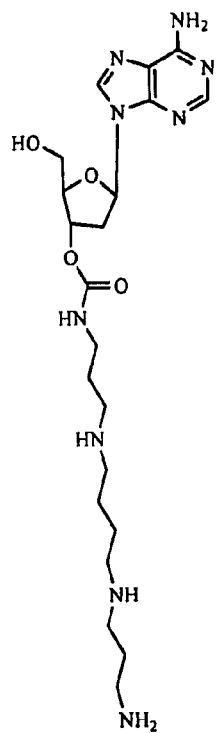

COLUMN 26
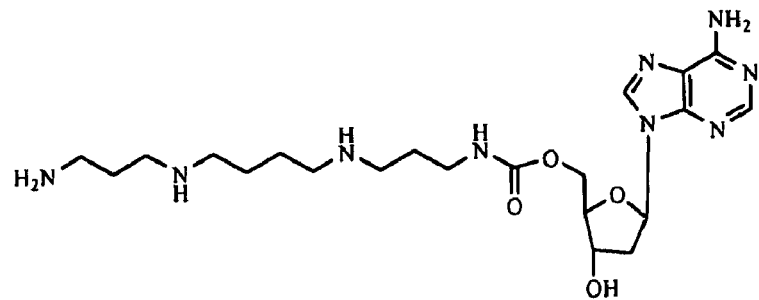

COLUMN 27
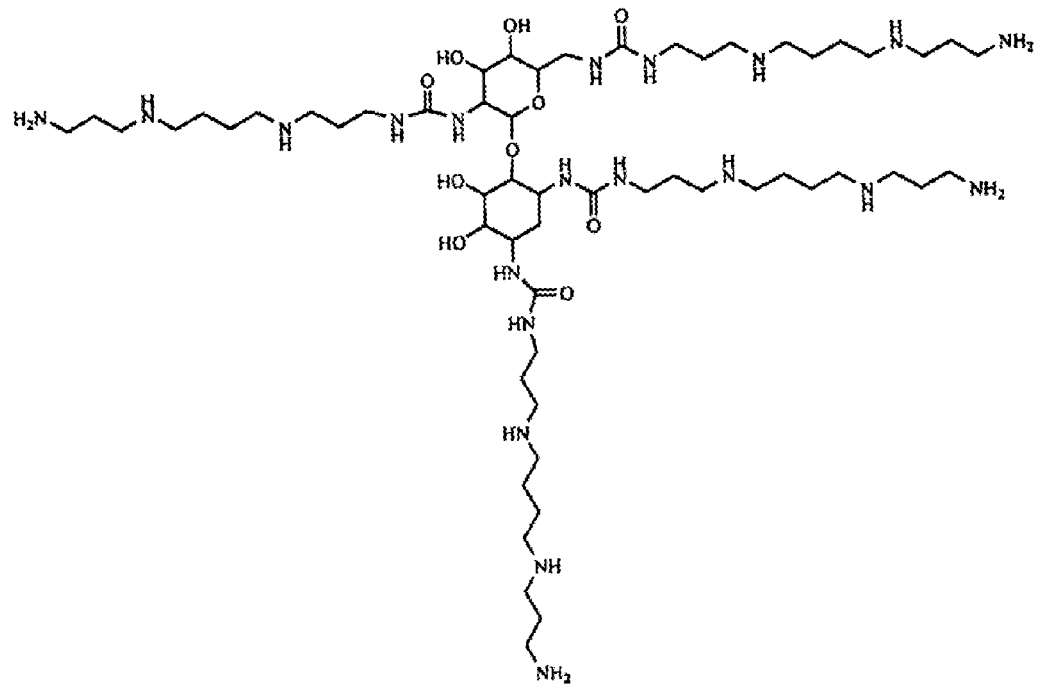

COLUMN 28
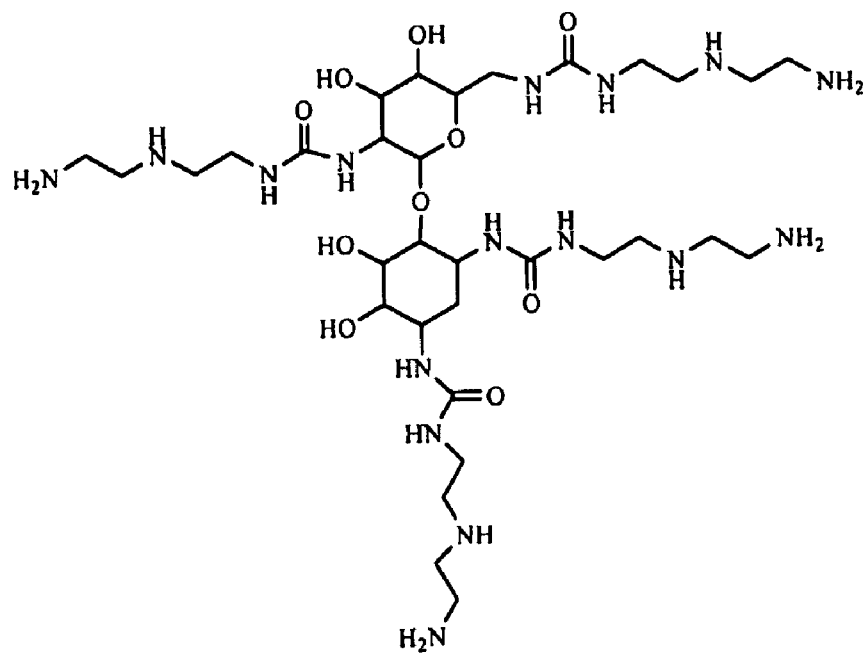

COLUMN 28
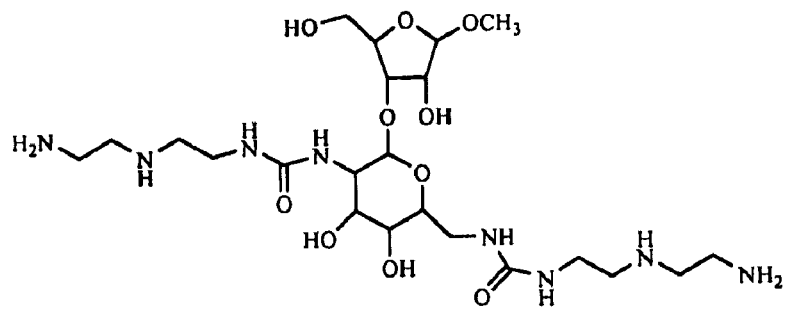

COLUMN 28
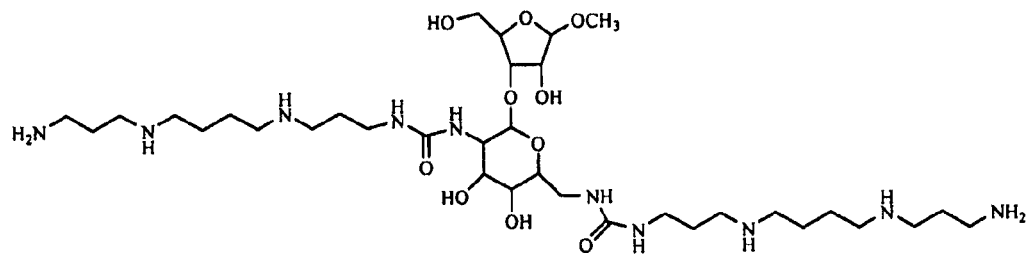

COLUMN 29
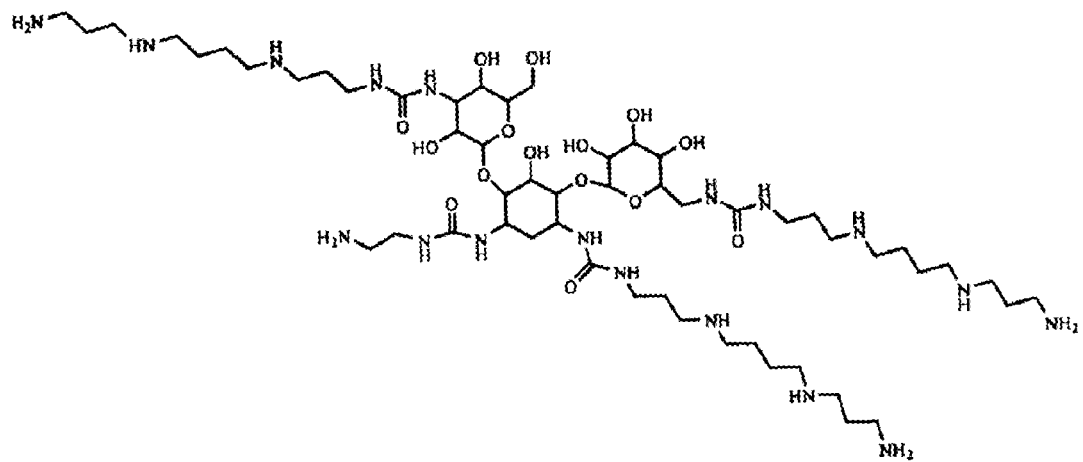

The invention claimed is:

1. A derivative of a carbohydrate compound, said derivative selected from

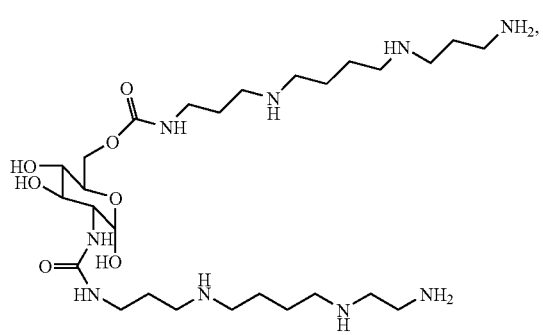

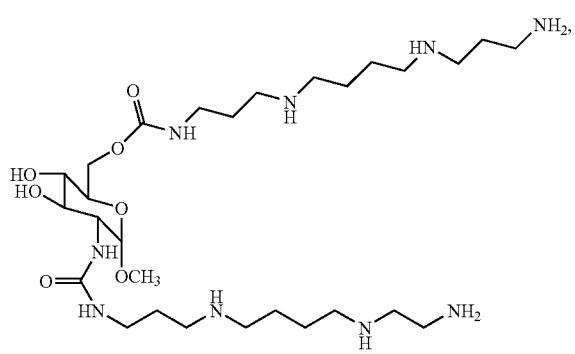

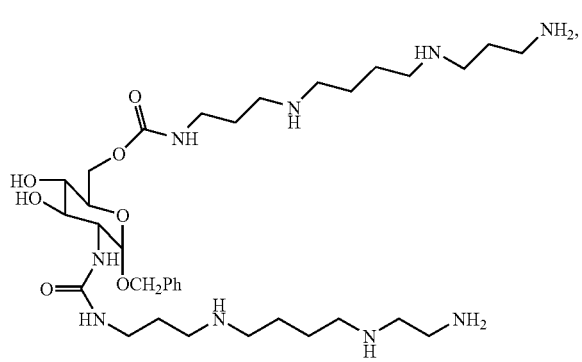

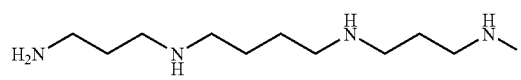

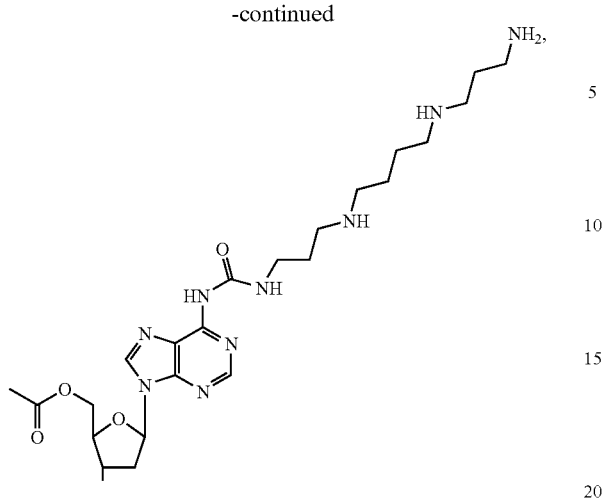
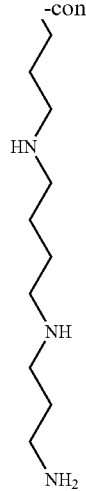
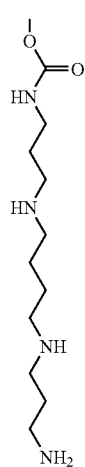
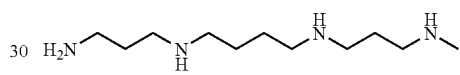
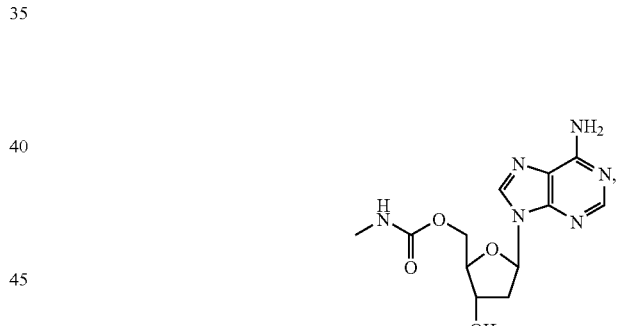
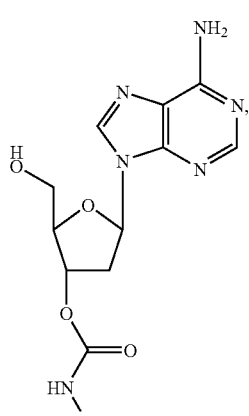
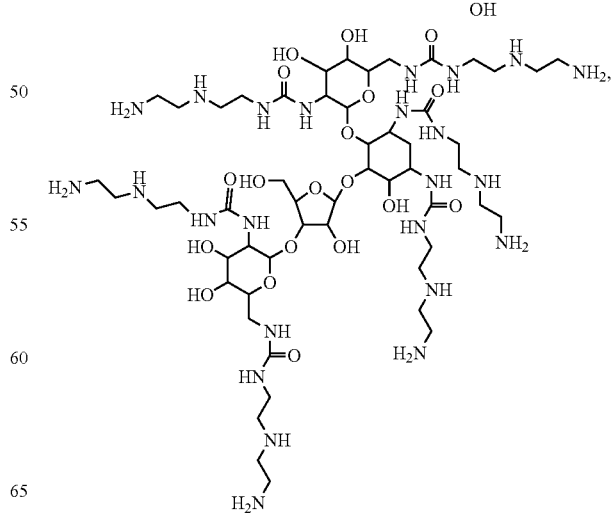

27
-continued
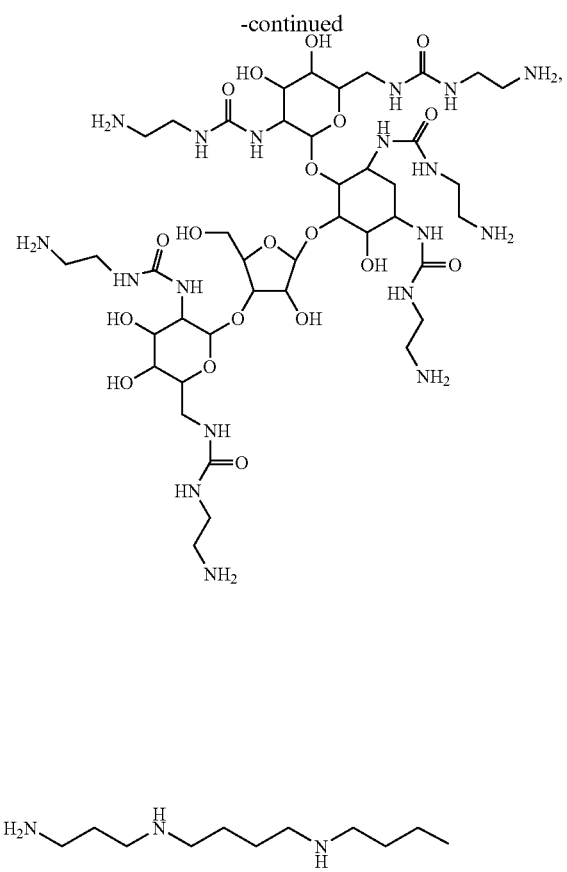
28
-continued
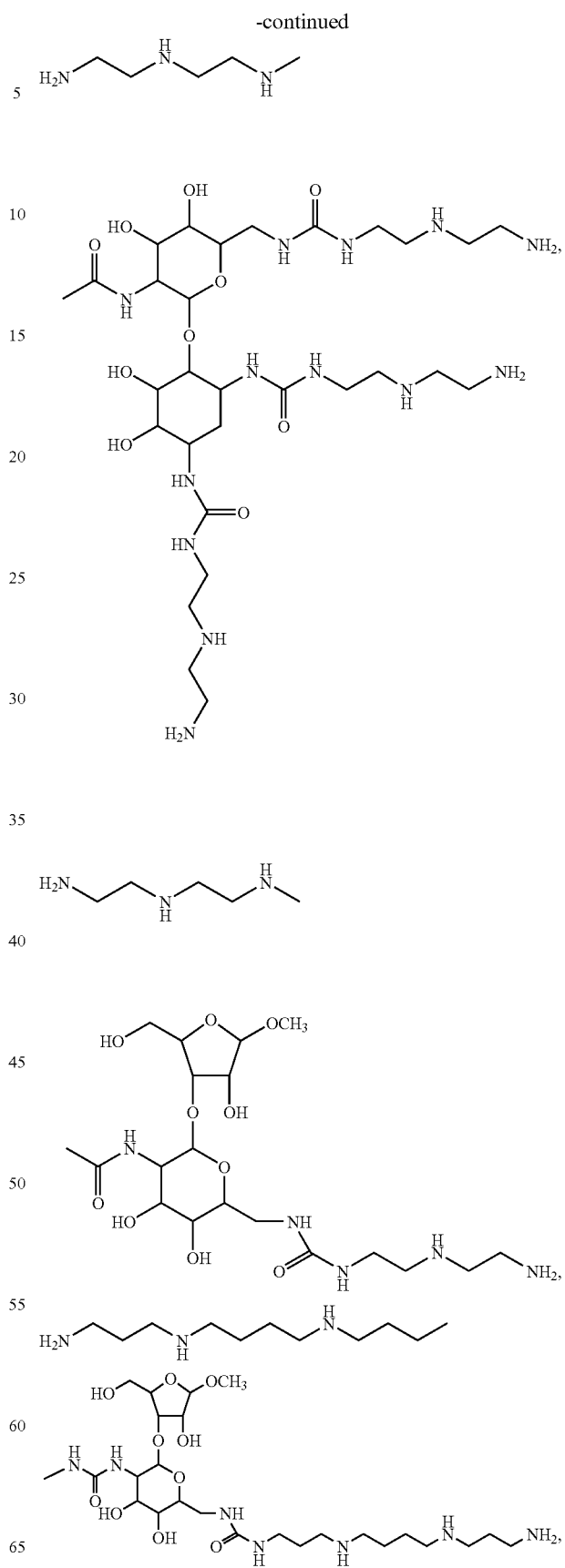

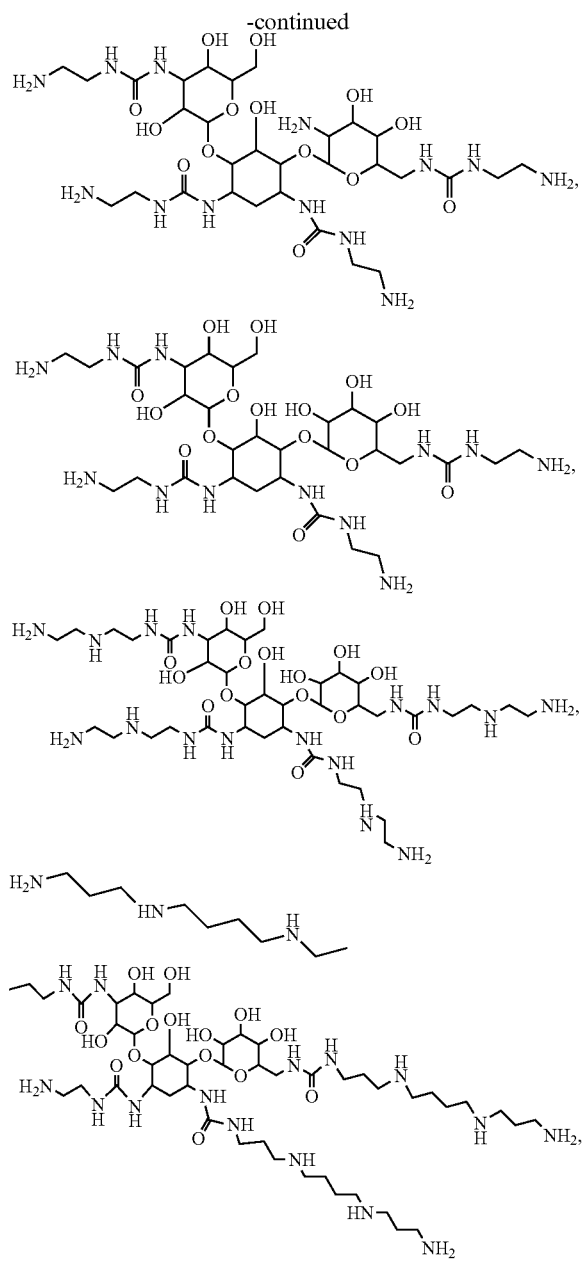

2. A method for separating one or more components of a biomolecule mixture by means of an ion exchange chromatographic system operated in the displacement mode, said method comprising: sequentially perfusing the system with a first solution comprising the biomolecule mixture, and a second solution comprising a derivative of a carbohydrate compound according to claim 1.

3. A method for separating a protein or peptide mixture by means of an ion exchange chromatographic system operated in the displacement mode, said method comprising: sequentially perfusing the system with a first solution comprising said mixture, and a second solution comprising a derivative of a carbohydrate compound according to claim 1.

4. The method according to claim 1, wherein the concentration of the derivative of a carbohydrate compound in the second solution is less than 5 mM.

5. A method for condensing DNA, said method comprising:
   combining DNA with at least one derivative of a carbohydrate compound according to claim 1, wherein the DNA is bound to the derivative of the carbohydrate compound.

* * * * *

UNITED STATES PATENT AND TRADEMARK OFFICE
CERTIFICATE OF CORRECTION

| | | |
|---|---|---|
| PATENT NO. | : 7,439,343 B2 | Page 1 of 11 |
| APPLICATION NO. | : 11/217193 | |
| DATED | : October 21, 2008 | |
| INVENTOR(S) | : Rege et al. | |

It is certified that error appears in the above-identified patent and that said Letters Patent is hereby corrected as shown below:

In the Specifications:

Scheme 4, Column 17: Delete "lines 1 - 43" and insert -- enclosed structure (Column 17) -- (Attached)

In the Claims:

Claim 1, Col. 24-25: Delete "lines 65 - 46" and insert -- enclosed structures (Columns 24-25, page 2) -- (Attached)

Claim 1, Col. 25-26: Delete "lines 51-65 and 1-20" and insert -- enclosed structures (Column 25-26, page 3) -- (Attached)

Claim 1, Col. 26: Delete "lines 30-48" and insert -- enclosed structures (Column 26, page 4) -- (Attached)

Claim 1, Col. 27: Delete "lines 31-65" and insert -- enclosed structures (Column 27, page 5) -- (Attached)

Claim 1, Col. 28: Delete "lines 1-33" and insert -- enclosed structures (Column 28, page 6) -- (Attached)

Claim 1, Col. 28: Delete "lines 37-54" and insert -- enclosed structures (Column 28, page 7) -- (Attached)

Claim 1, Col. 28: Delete "lines 55-65" and insert -- enclosed structures (Column 28, page 8) -- (Attached)

UNITED STATES PATENT AND TRADEMARK OFFICE
CERTIFICATE OF CORRECTION

PATENT NO. : 7,439,343 B2
APPLICATION NO. : 11/217193
DATED : October 21, 2008
INVENTOR(S) : Rege et al.

It is certified that error appears in the above-identified patent and that said Letters Patent is hereby corrected as shown below:

Claim 1, Col. 29: Delete "lines 35-50" and insert -- enclosed structures (Column 29, page 9) -- (Attached)

Signed and Sealed this

Tenth Day of March, 2009

JOHN DOLL
*Acting Director of the United States Patent and Trademark Office*